US008875893B2

(12) United States Patent
Min

(10) Patent No.: US 8,875,893 B2
(45) Date of Patent: Nov. 4, 2014

(54) MEDICAL CONTAINERS FOR USE IN BLOOD COLLECTION AND PROCESSING AND MEDICAL SYSTEMS, METHODS AND APPARATUS FOR USE IN BLOOD COLLECTION AND PROCESSING

(75) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 334 days.

(21) Appl. No.: 13/021,310

(22) Filed: Feb. 4, 2011

(65) Prior Publication Data

US 2011/0192745 A1 Aug. 11, 2011

Related U.S. Application Data

(60) Provisional application No. 61/301,687, filed on Feb. 5, 2010.

(51) Int. Cl.

*B65D 69/00* (2006.01)
*B65D 71/00* (2006.01)
*A61J 1/10* (2006.01)
*A61M 1/02* (2006.01)
*A61M 1/36* (2006.01)

(52) U.S. Cl.

CPC ................ *A61J 1/10* (2013.01); *A61M 1/0209* (2013.01); *A61M 1/3693* (2013.01); *A61M 2205/6072* (2013.01)

USPC .......................................... 206/570; 206/564

(58) Field of Classification Search

CPC ...... A61F 2/0095; B65D 69/00; B65D 71/00; B65D 71/0014

USPC ......... 206/570, 561, 569, 363, 370, 446, 477, 206/486, 464, 465, 503, 504, 562, 564, 206/438; 220/529, 552, 528; 604/408, 6.15, 604/403, 410

See application file for complete search history.

(56) References Cited

U.S. PATENT DOCUMENTS

| | | | | |
|---|---|---|---|---|
| 2,827,093 | A * | 3/1958 | Shenfield et al. | 150/112 |
| 3,752,385 | A * | 8/1973 | Woodgate | 229/120.07 |
| 4,284,209 | A | 8/1981 | Barbour, Jr. | |
| 4,479,762 | A * | 10/1984 | Bilstad et al. | 417/395 |
| 4,679,693 | A * | 7/1987 | Forman | 383/203 |
| 4,753,739 | A | 6/1988 | Noble | |
| 4,838,872 | A | 6/1989 | Sherlock | |
| 4,892,668 | A | 1/1990 | Harmony et al. | |

(Continued)

FOREIGN PATENT DOCUMENTS

| | | |
|---|---|---|
| DE | 19537271 A1 | 4/1997 |
| EP | 1048305 | 11/2000 |

(Continued)

*Primary Examiner* — Luan K Bui
*Assistant Examiner* — Rafael Ortiz
(74) *Attorney, Agent, or Firm* — Cook Alex Ltd.

(57) ABSTRACT

Medical containers for use in blood collection and processing and medical systems, methods and apparatus for use in blood collection and processing are described. An example medical container to be used during blood collection and processing, the medical container includes an elongated body defining a compartment and a base coupled at a first end of the elongated body. Additionally, the medical container includes a divider extending through the compartment to separate the compartment into a first subcompartment and a second subcompartment, the divider comprising a first material and the elongated body comprising a second material, the first material being relatively more rigid than the second material, the first subcompartment and the subsecond compartment each to accommodate blood pack components.

30 Claims, 22 Drawing Sheets

100 202 206 208 212 216 110 204 214 218 224 210 218 220 220 106 222 102 108

(56) References Cited

U.S. PATENT DOCUMENTS

| | | | | |
|---|---|---|---|---|
| 4,896,772 | A * | 1/1990 | Walter et al. | 206/484.2 |
| 4,927,024 | A * | 5/1990 | Lloyd | 206/562 |
| 5,100,564 | A | 3/1992 | Pall et al. | |
| 5,543,062 | A | 8/1996 | Nishimura | |
| 5,620,069 | A * | 4/1997 | Hurwitz | 190/107 |
| 5,632,906 | A | 5/1997 | Ishida et al. | |
| 5,690,815 | A * | 11/1997 | Krasnoff et al. | 210/97 |
| 5,863,436 | A | 1/1999 | Matkovich | |
| 6,053,885 | A | 4/2000 | Beshel | |
| 6,171,493 | B1 | 1/2001 | Zia et al. | |
| 6,358,420 | B2 | 3/2002 | Blickhan et al. | |
| 6,688,935 | B1 * | 2/2004 | Lin | 446/15 |
| 7,041,076 | B1 * | 5/2006 | Westberg et al. | 604/6.01 |
| 7,059,429 | B2 * | 6/2006 | Taylor et al. | 175/57 |
| 7,644,823 | B2 * | 1/2010 | Gelardi et al. | 206/776 |
| 7,993,531 | B2 | 8/2011 | Oleskiewicz et al. | |
| 2002/0151423 | A1 * | 10/2002 | Jorgensen et al. | 494/21 |
| 2003/0004453 | A1 | 1/2003 | Goudaliez et al. | |
| 2003/0104349 | A1 | 6/2003 | Bischof et al. | |
| 2005/0252821 | A1 * | 11/2005 | Azzolini et al. | 206/570 |
| 2006/0278690 | A1 * | 12/2006 | Wang | 229/120.33 |
| 2007/0241154 | A1 * | 10/2007 | Potts et al. | 224/539 |
| 2008/0083629 | A1 * | 4/2008 | Soucie | 206/170 |
| 2008/0156728 | A1 | 7/2008 | Blickhan et al. | |
| 2011/0155600 | A1 * | 6/2011 | Hudson | 206/427 |

FOREIGN PATENT DOCUMENTS

| | | | |
|---|---|---|---|
| EP | 1938850 | A1 | 7/2008 |
| WO | WO 96/39940 | A1 | 12/1996 |
| WO | WO 02/11855 | A1 | 2/2002 |

* cited by examiner

MEDICAL CONTAINERS FOR USE IN BLOOD COLLECTION AND PROCESSING AND MEDICAL SYSTEMS, METHODS AND APPARATUS FOR USE IN BLOOD COLLECTION AND PROCESSING

RELATED APPLICATION

This patent claims priority to U.S. Provisional Patent Application No. 61/301,687 filed Feb. 5, 2010, which is hereby incorporated herein by reference in its entirety.

TECHNICAL FIELD

The present patent pertains to containers and, more particularly, to medical containers for use in blood collection and processing and medical systems, methods and apparatus for use in blood collection and processing.

BACKGROUND

Blood packs may be used during blood collection and/or processing. A blood pack may include a needle fluidly coupled to a primary blood collection container. Additionally, the blood pack may include a plurality of transfer bags and a container containing a red blood cell preservative solution all, or some of which, may be fluidly coupled to the primary blood collection container. In practice, whole blood may be transferred from a donor via the needle to the primary blood collection container. Once the whole blood has been collected, a plurality of blood packs containing whole blood may be loaded into a centrifuge to separate plasma from red blood cells, for example. Plasma may then be transferred from the primary collection container to one of the transfer bags and the red blood cells may be transferred to another one of the transfer bags after leukoreduction.

DETAILED DESCRIPTION

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The examples described herein relate to medical containers in which blood packs may be conveniently stored and/or protected during blood collection and processing. In contrast to known techniques, the examples described herein reduce and/or eliminate the need for off-chart recording. The examples described herein enable blood packs to be balanced using portions of the medical containers themselves, thereby expediting the balancing process prior to centrifugation. The medical containers described herein are sized and/or shaped to correspond to cups of known centrifuges. Such an approach of having the medical containers sized to correspond to the cups of known centrifuges, increases the speed in which blood packs may be loaded and/or unloaded into centrifuges and/or processed generally. Additionally, because the blood packs are housed at least partially within the example medical containers during a majority of blood collecting and processing, accidents are less likely to occur in which a blood pack breaks and/or an interface between red blood cells and plasma is disrupted during handling and/or centrifugation.

Example triage systems are described in which the example medical containers may be automatically sorted based on information on the medical containers. By automatically sorting the medical containers, blood centers may more efficiently identify blood that has less time until expiration.

Example expressors are described in which the example medical containers may be positioned and compressed to force different blood components from the bags contained therein. By compressing the medical container itself, the bag containing whole blood may not have to be removed from the medical container during processing. Additionally or alternatively, the example expressors may include a pump that pumps red blood cells through a filter during a leukoreduction process.

Figure 1A:
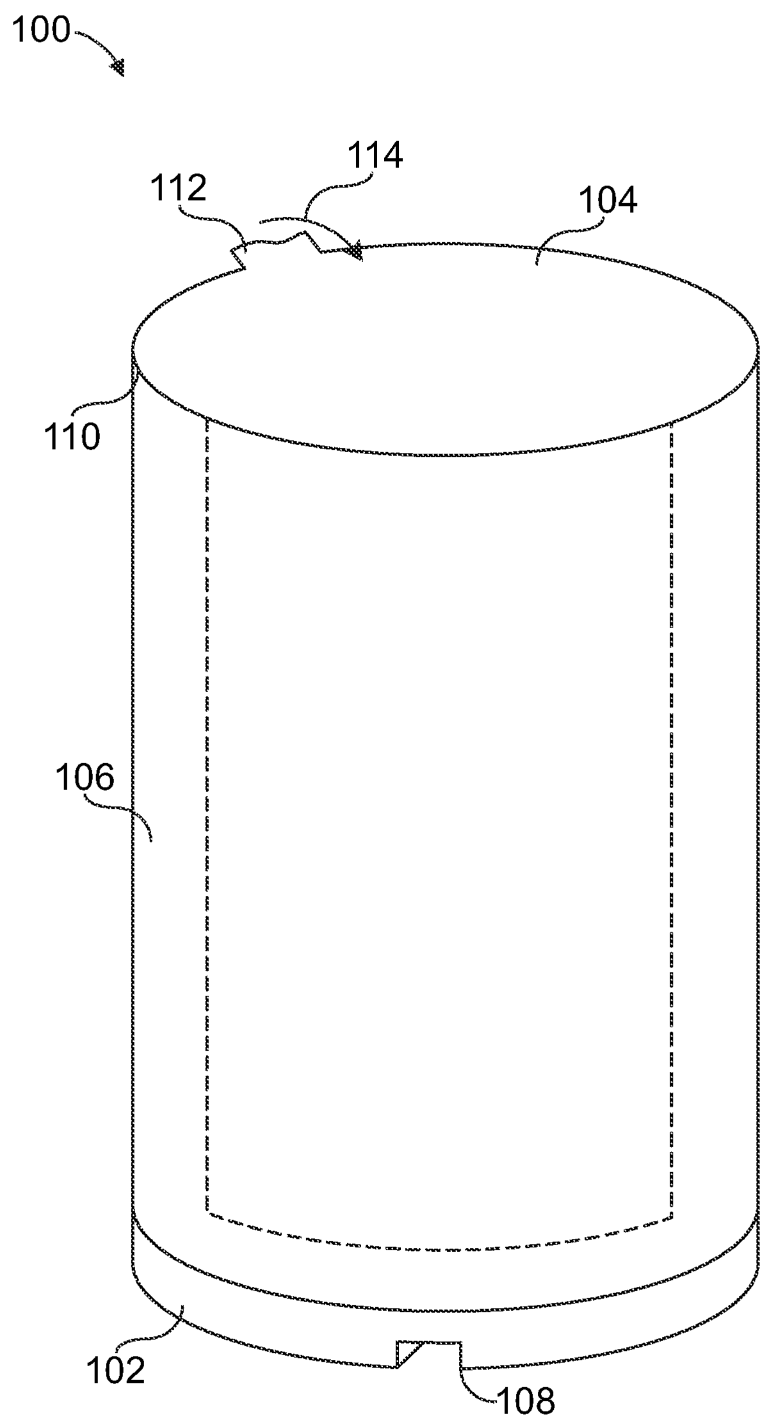
FIG. 1A depicts an example medical container with a lid.
Figure 1B:
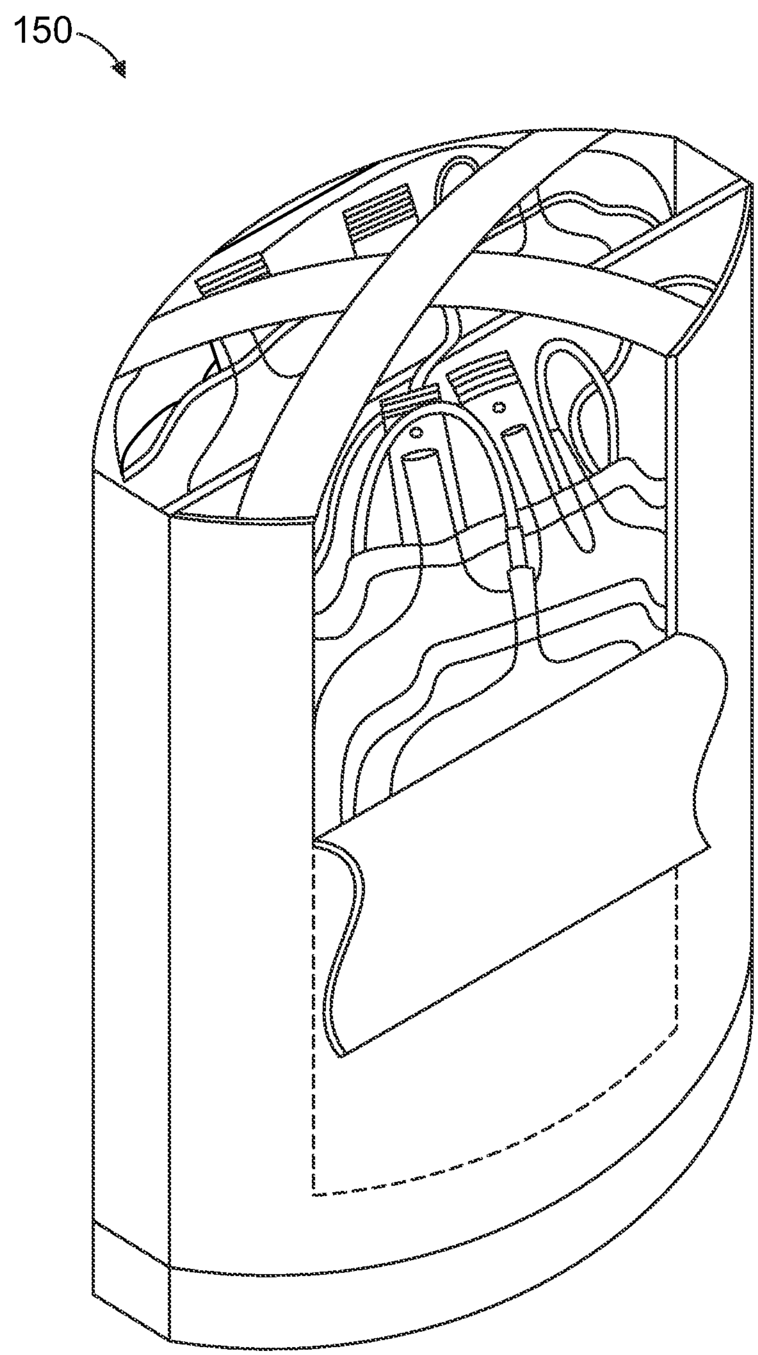
FIG. 1B depicts an alternative medical container.

FIG. 1A depicts an example medical container or prepackaged blood pack 100 for use in the medical industry to collect and process blood and/or blood components, for example. The container includes a base 102, a lid 104 (e.g., a peelable seal) and an elongated body 106. The base 102 may be made of a relatively rigid material such as a plastic material. The base 102 defines a notch or key 108 to enable the medical container 100 to be secured relative to another apparatus (not shown) and may have a shape (e.g., a circular shape as depicted by the medical container 100 of FIG. 1A, an oval shape as depicted by an example medical container 150 of FIG. 1B or an oblong shape) that corresponds to a cup (not shown) of a centrifuge (not shown). The elongated body 106 may be made of a relatively deformable, elastic and/or flexible material such as a foil based material or a plastic material, for example.

The lid 104 may be removably coupled to a surface 110 of the elongated body 106 to substantially prevent contaminates from entering the medical container 100, for example. The lid 104 may be made of any suitable material such as an aluminum lidding foil or a plastic material and may be removably coupled to the elongated body 106 by an adhesive (e.g., sealing lacquer) or by heat sealing, for example. In practice, a person may grasp a tab 112 of the lid 104 and exert a force in a direction generally represented by arrow 114 to remove the lid 104 from the medical container 100. While the medical container 100 of FIG. 1A includes the lid 104 having the tab 112, the medical container 100 may not be provided with the lid 104 and/or the lid 104 may not include the tab 112.

Figure 2:
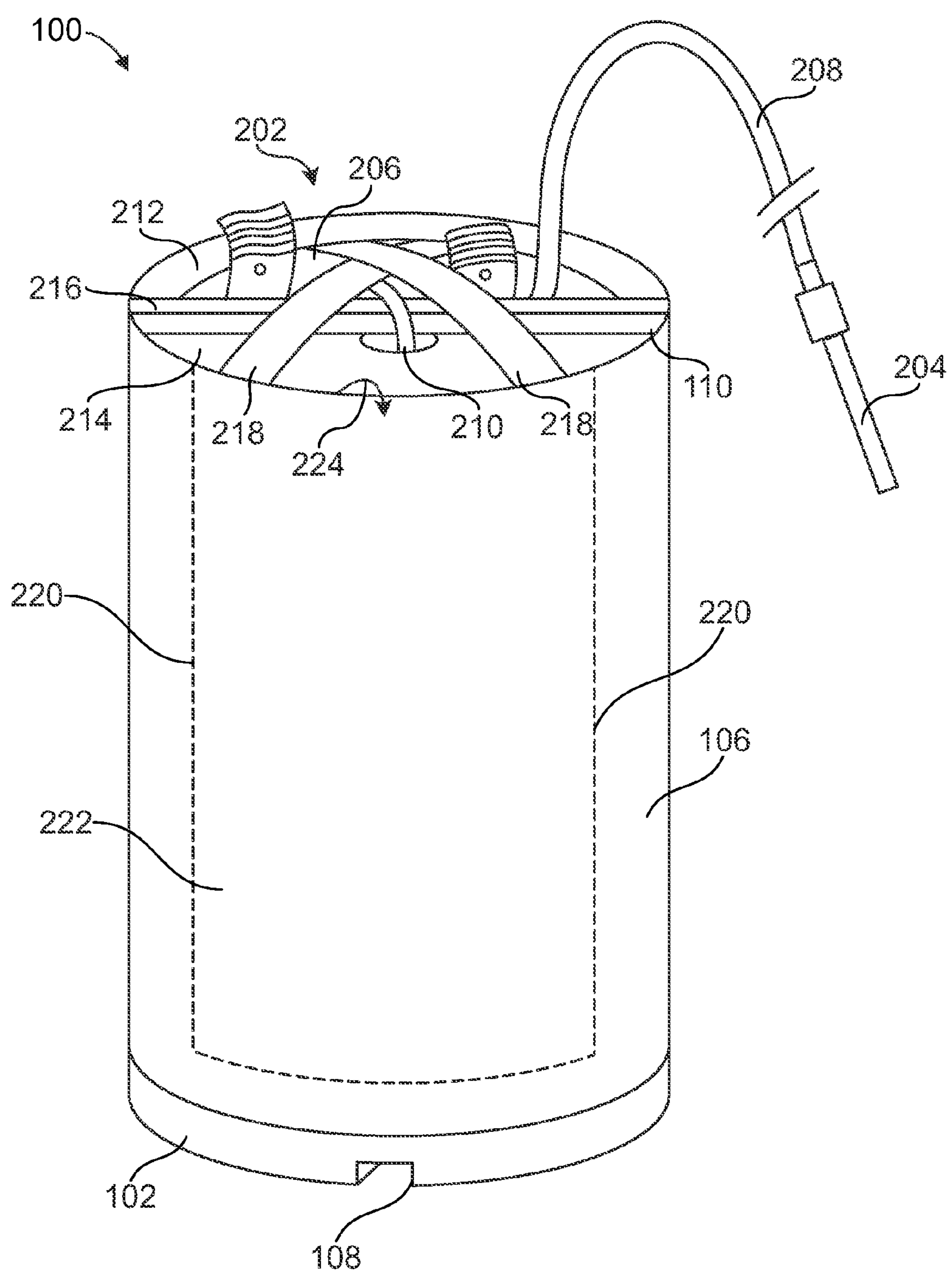
FIG. 2 depicts the example medical container of FIG. 1A with the lid removed.

FIG. 2 depicts the medical container 100 of FIG. 1A in which the lid 104 has been removed. A blood pack 202 may be housed or positioned in the medical container 100. The blood pack 202 may include a needle 204, a primary blood collection container or container 206, a plurality of transfer containers or bags (not shown), a filter (e.g., a leukocyte filter) (not shown) and a container containing a preservative solution (e.g., Adosol®) (not shown). The container 206 may contain an anticoagulant and may be fluidly coupled to the needle 204 via a tube 208. In some examples, the container 206, the plurality of transfer containers, the filter and the container containing the preservative solution may be fluidly coupled together via a tube 210 and/or other tubes (not shown).

To separate a first storage compartment 212 from a second storage compartment 214, the medical container 100 includes a divider or middle frame 216. The divider 216 may be made of a relatively rigid material and may extend toward and be coupled to the base 102 to increase the structural rigidity of the medical container 100.

In some examples, a plurality of straps 218 may retain the container 206 in the first storage compartment 212 and may retain the plurality of transfer containers, the filter and the container containing the preservative solution in the second storage compartment 214. Additionally, the straps 218 may be utilized as a handle to move and/or carry the medical container 100 during blood collection and/or processing, for example.

To enable access to the second storage compartment 214 during blood processing, the elongated body 106 defines a perforation and/or tearable portion (e.g., a breakaway portion) 220. To detach or partially detach a portion or section 222 of the elongated body 106 from the medical container 100, a person may exert a force on the portion 222 in a direction generally represented by arrow 224 to initiate a tear adjacent the perforation 220. Once initiated, the person may continue to detach the portion 222 along the perforation 220, thereby providing access to the second storage compartment 214.

Figure 3:
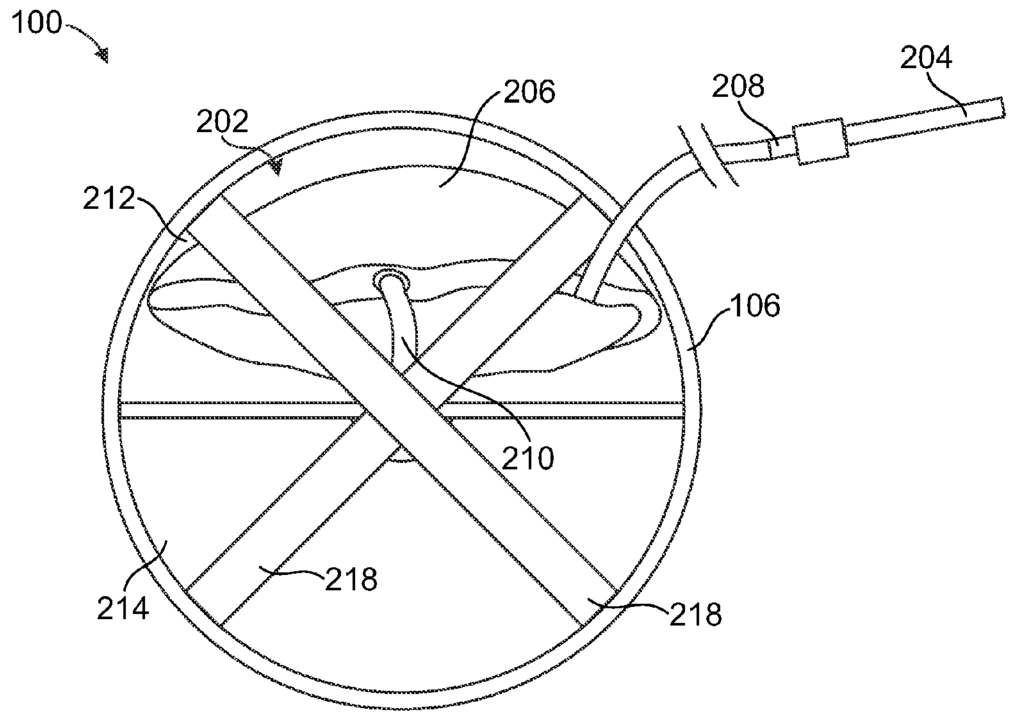
FIG. 3 depicts a top view of the example medical container of FIG. 2.
Figure 4:
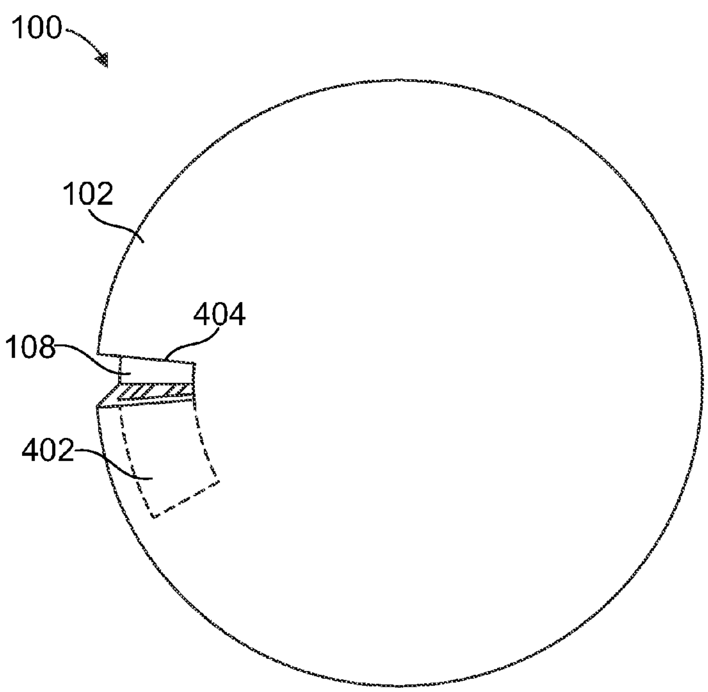
FIG. 4 depicts a bottom view of the example medical container of FIG. 2.

FIG. 3 depicts a top view of the medical container 100 and FIG. 4 depicts a bottom view of the medical container 100. Turning to FIG. 4, in some examples, the notch 108 includes a recessed or slotted portion 402 that accepts a lock or L-shaped lock to secure the medical container 100 relative to another apparatus (not shown). In practice, a person may position the medical container 100 such that the L-shaped lock enters an opening 404 of the notch 108. The person may then rotate the medical container 100 such that a portion (not shown) of the L-shaped lock (not shown) enters the slotted portion 402, thereby securing the medical container 100 relative to the other apparatus.

Figure 5:
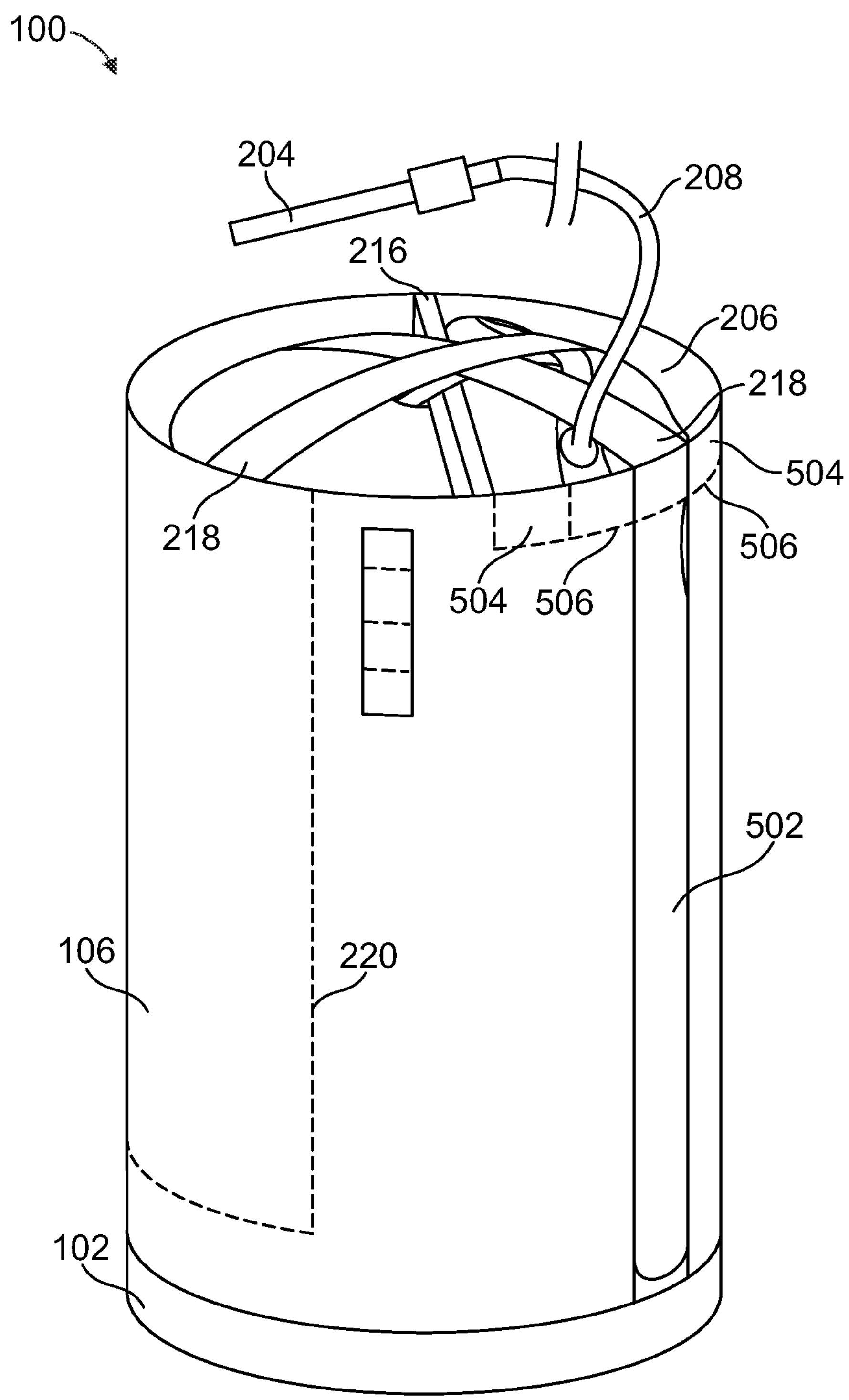
FIGS. 5 and 6 depict alternative views of the example medical container of FIG. 1A.
Figure 6:
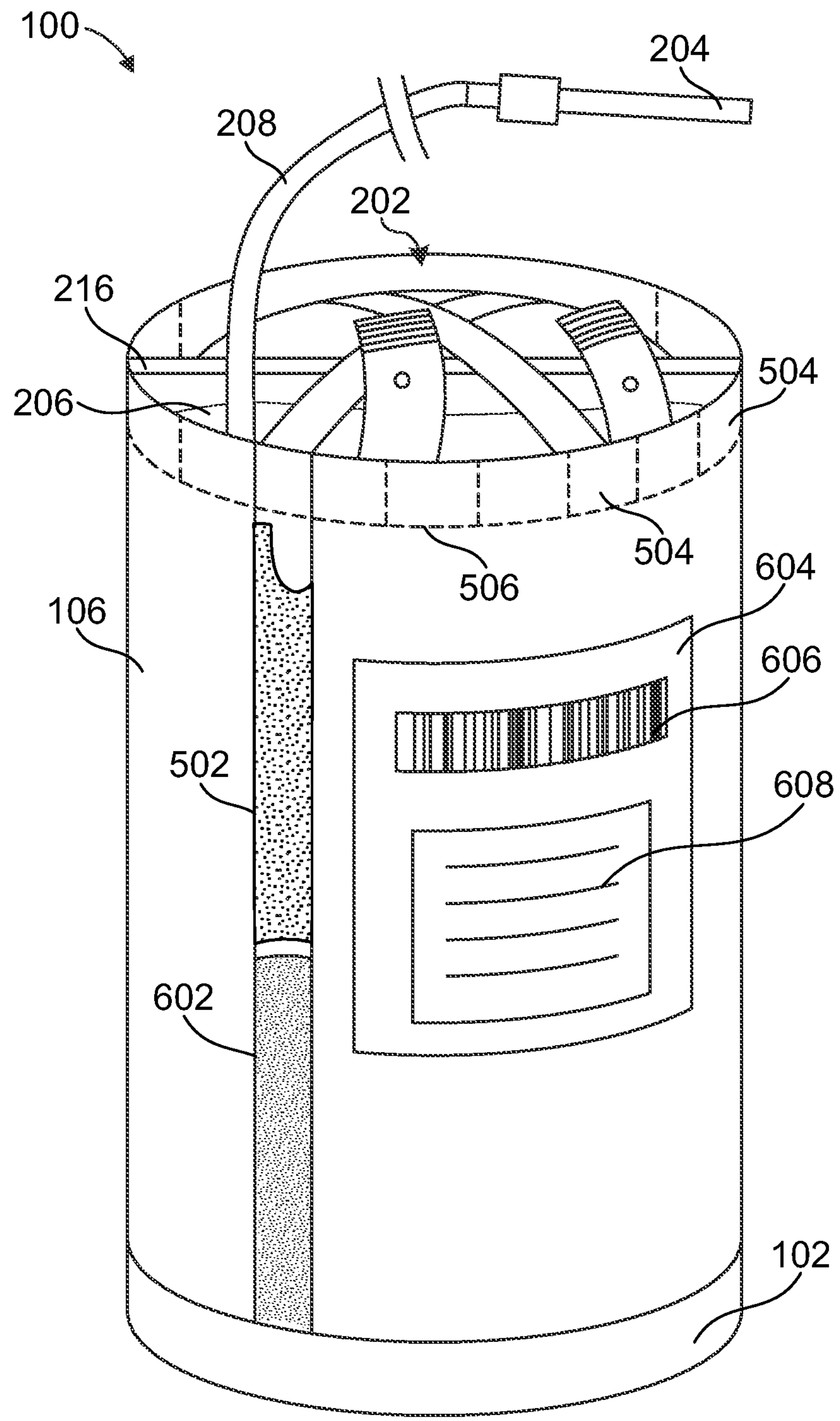

FIGS. 5 and 6 depict alternative views of the medical container 100. Turning to FIG. 5, the elongated body 106 may include a window or substantially transparent portion 502 to enable a person to visually identify an amount of fluid (e.g., blood) within the container 206, for example. The window 502 may be made of a plastic material or any other suitable material that may be similar or different from the material of the remainder of the elongated body 106.

Additionally or alternatively, to enable the weight of the medical container 100 containing blood to be relatively easily and/or quickly balanced with another container (not shown) containing blood prior to centrifugation, the elongated body 106 may include a plurality of removable tabs 504 adjacent the surface 110. The removable tabs 504 may have a predetermined weight of approximately 1.0 grams; however, any other suitable weight may be used instead (e.g., 0.5 grams, 1.0 grams, 1.5, grams, etc.). All of the removable tabs 504 may have similar weights or some or all of the removable tabs 504 may have different weights. A perforation or tearable portion 506 may at least partially surround each of the removable tabs 504 to enable the tabs 504 to be relatively easy removed.

FIG. 6 depicts the medical container 100 including fluid (e.g., blood) 602 that can be seen through the window 502. Additionally, the medical container 100 includes a processing label (e.g., a customized label) 604 affixed to the elongated body 106. Because the processing label 604 is affixed to the medical container 100 (e.g., not a final blood component) and not to any of the components of the blood pack 202 (e.g., a final blood component), the information included on and/or other characteristics (e.g., size) of the processing label 604 may be exempt from blood industry, ISBT 128 and/or the Food and Drug Administration (FDA) regulation. Thus, additional or different information may be included on the processing label 604 than if the processing label 604 was affixed directly to the blood pack 202 itself.

The processing label 604 may include a bar code 606 and a portion 608 where additional information may be included and/or written, for example. Some information that may be included on the processing label 604 may be the time that the blood was collected, the start time of blood collection, the end time of blood collection, an identifier associated with an operator (e.g., a nurse), a donor identification number (DIN), donor gender and/or weight of the blood collected, for example. The processing label 604 may include a plurality identical portions that may be removed and/or pealed off and affixed to another container (e.g., a transfer bag), for example.

Figure 7:
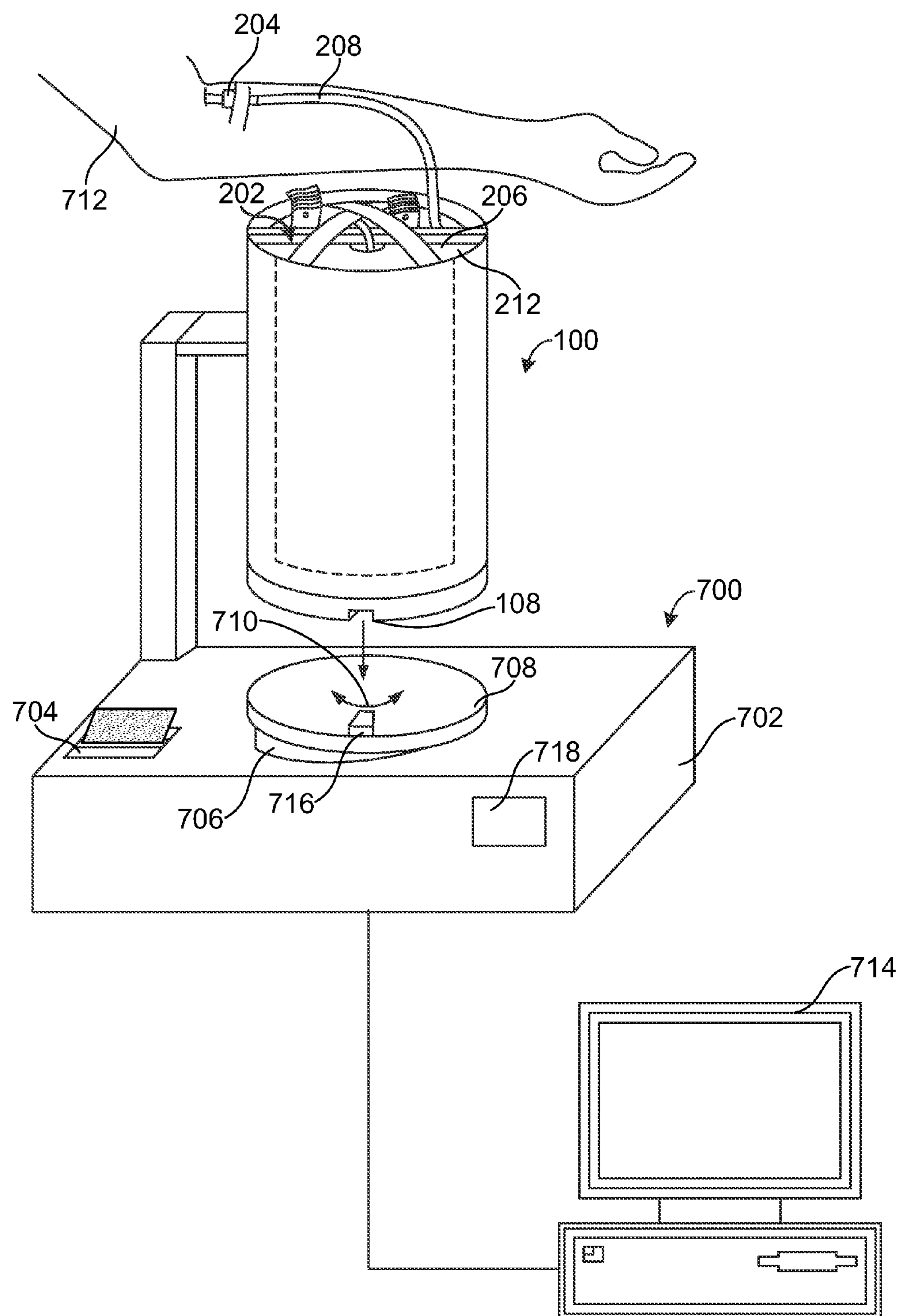
FIGS. 7 and 8A depict the example medical container of FIG. 1A and an apparatus used during blood collection.
Figure 8A:
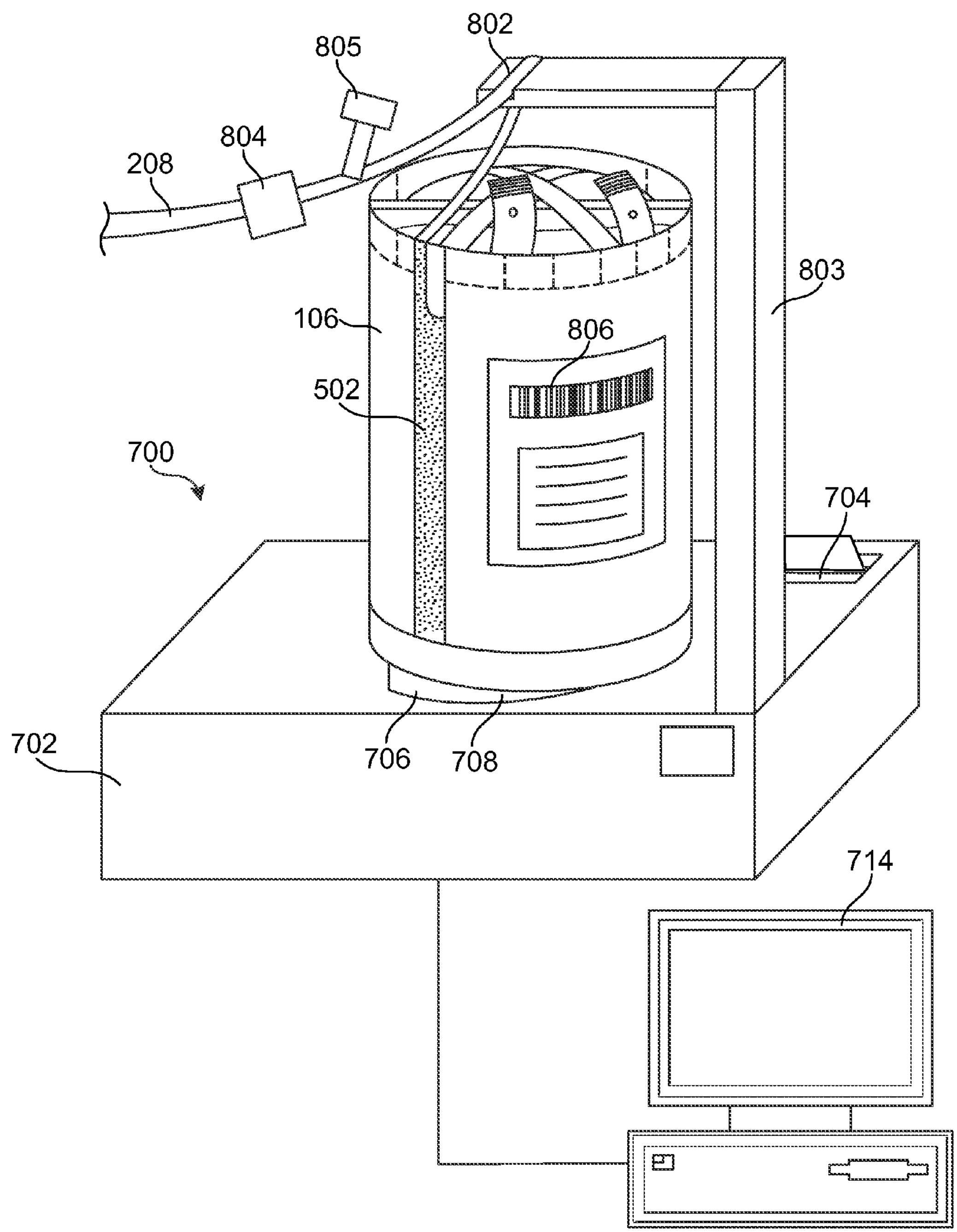

FIGS. 7 and 8A depict the medical container 100 and an apparatus 700 that can be used during blood collection. The apparatus 700 includes a base 702 having a printer 704 that may be configured to print labels associated with the medical container 100. Additionally, the apparatus 700 includes a weight scale 706 to measure the weight of the medical container 100 and a plate 708 onto which the base 102 is to be positioned. The plate 708 may be coupled (e.g., mechanically coupled) to a motor or other device (not shown) to agitate, oscillate and/or move the plate 708 back and forth in a direction generally represented by arrow 710. This agitation enables anticoagulant contained within the container 206 to be mixed with blood entering the container 206, for example.

In practice, an operator (e.g., a nurse or technician) may initially enter information associated with the donor, the operator and/or the blood collection into the apparatus 700. In some examples, this information may be entered into a computer, processor or other data entry device 714 communicatively coupled to the apparatus 700. While the computer 714 is depicted as separate from the apparatus 700, the computer 714 may be incorporated into the apparatus 700 and/or the apparatus 700 may not be provided with the computer 714. The operator may then remove the lid 104 (FIG. 1A) from the medical container 100 and position the medical container 100 such that the notch 108 interacts and/or interfaces with a lock or L-shaped lock 716 of the plate 708 to secure the medical container 100 relative to the apparatus 700. The operator may then remove the needle 204 and the tube 208 from the first storage compartment 212 and secure the tube 208 in a clamp 802 (FIG. 8A) supported by a frame 803 (FIG. 8A) of the apparatus 700. The clamp 802 may be communicatively coupled to the weight scale 706 via the computer 714 and/or the apparatus 700 such that once the medical container 100 weighs a predetermined amount (e.g., a predetermined amount of blood has been collected from the donor), a signal may be transmitted to the clamp 802 causing the clamp 802 to close.

After the needle 204 has been inserted into a donor's arm 712, blood may begin to flow through the tube 208 and into the container 206 and the plate 708 may move and/or agitate, thereby mixing the anticoagulant with the blood. In some examples, the blood may be pumped from the donor's arm 712 using a pump 804 (e.g., peristaltic pump) that may be communicatively coupled the apparatus 700. To monitor the pressure (e.g., vein pressure) of the blood flowing through the tube 208, the apparatus 700 may include a sensor (e.g., a pressure sensor) 805 that may be communicatively coupled to the apparatus 700. Depending on the pressure sensed by the sensor 805 and communicated to the apparatus 700, a signal may be transmitted to the pump 804 to change (e.g., increase or decrease) the rate at which blood is pumped from the donor's arm 712, for example.

As the blood enters the container 206, the weight scale 706 weighs the medical container 100 and the computer 714 and/or the apparatus 700 may determine whether or not a predetermined weight has been achieved. In other examples, the pump 804 may convey to the apparatus 700 the amount of blood that has been pumped and the computer 714 and/or the apparatus 700 may determine whether or not a predetermined amount and/or volume of blood has been collected. The predetermined weight and/or volume of blood may be associated with an amount of blood that a donor is to donate. If the computer 714 and/or the apparatus 700 determines that the predetermined weight has been achieved, a signal may be transmitted to the clamp 802 causing the clamp 802 to close, thereby preventing additional blood from being collected from the donor (e.g., preventing over-collection of whole blood), for example. The operator may then remove the needle 204 from the donor's arm 712 and press a button 718 initiating the printer 704 to print a processing label 806. Once printed, the processing label 806 may be affixed to the medical container 100. The use of the processing label 806 decreases and/or eliminates the need for off-chart recording because the information is contained on the processing label 806.

Figure 8B:
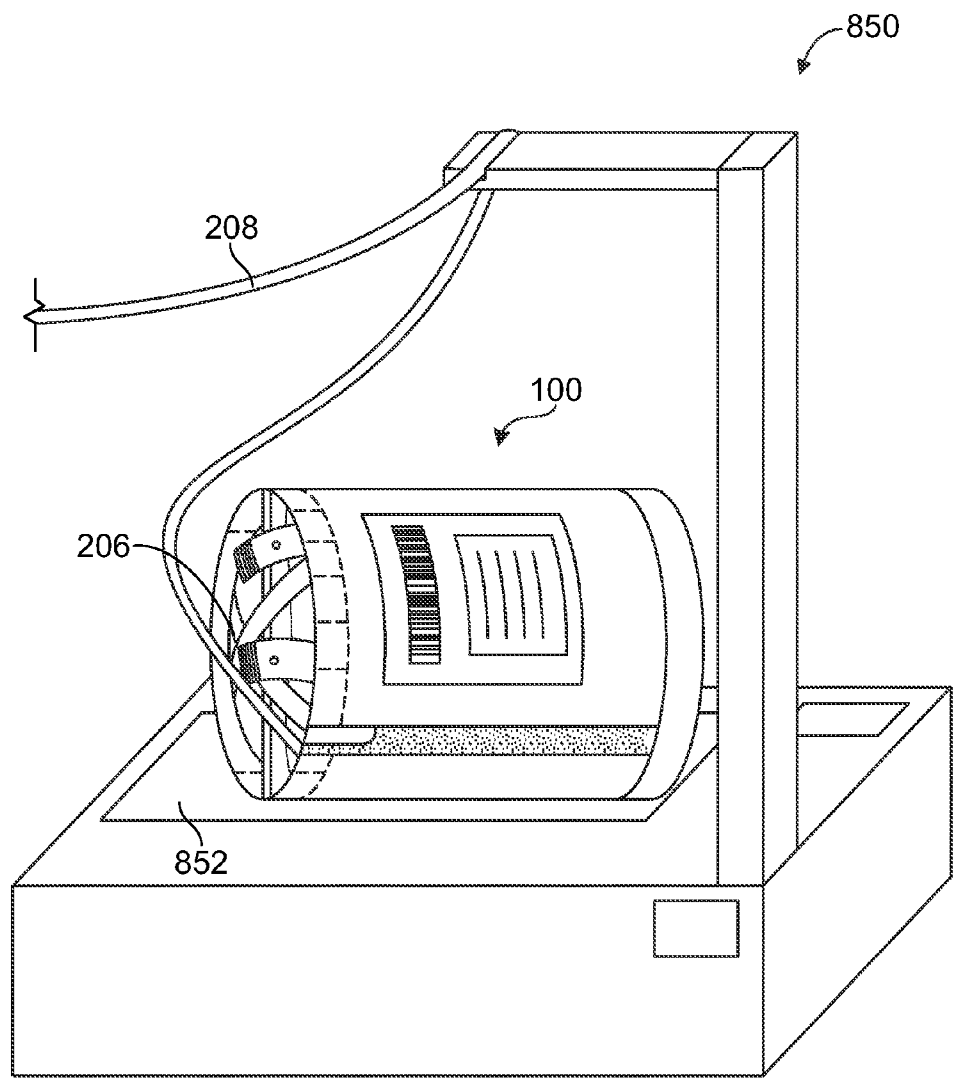
FIG. 8B depicts the example medical container of FIG. 1A and an alternative apparatus used during blood collection.

FIG. 8B depicts an example apparatus 850 that is substantially similar to the apparatus 700. However, instead of securing the medical container 100 to the apparatus 700 using the interaction between the notch 108 and the L-shaped lock 716, the medical container 100 is to be positioned on a bed or cradle 852. In operation, as blood flows through the tube 208 and into the container 206, the bed 852 may move and/or agitate to mix the anticoagulant with the blood.

Figure 9:
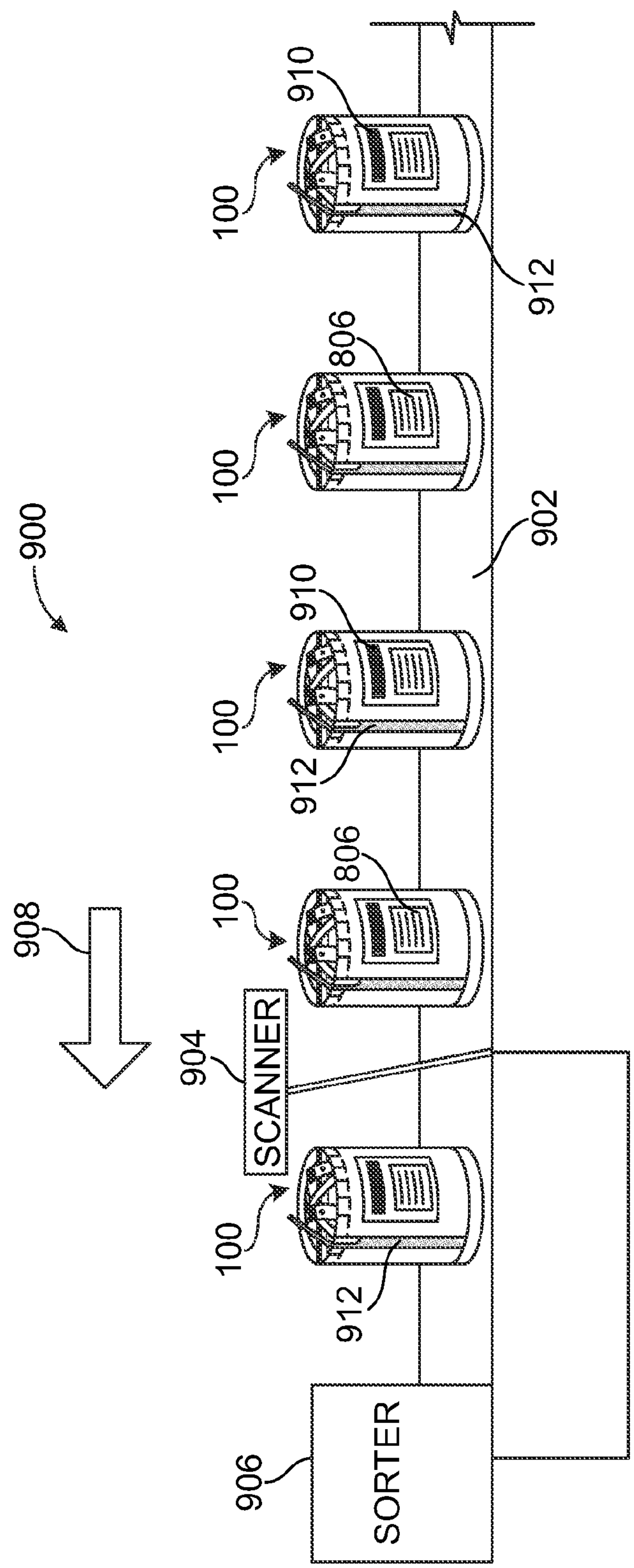
FIG. 9 depicts an example triage system.

FIG. 9 depicts an example triage system 900 including a conveyor 902, a scanner 904 and a sorter 906 that may be used in a blood center, for example. The sorter 906 may be communicatively coupled to the scanner 904 and may include a plurality of conveyors (not shown) that divert and/or sort the medical containers 100 depending on the urgency in which blood in the particular medical container 100 has to be processed, for example. However, the sorter 906 may sort and/or enable the medical containers 100 having higher priorities (e.g., less time until blood expiration) to be identified and/or accessed in any other suitable way. The medical containers 100 may include an identifier and/or be color coded to indicate how the blood in a particular medical container 100 will be processed. The identifiers and/or color coding may be positioned adjacent the processing label 806. Medical containers 100 containing blood that will be processed to produce RBCs and plasma may include a first color identifier (e.g., blue) and medical containers 100 containing blood that will be processed to produce platelets may include a second color identifier (e.g., green), for example.

The plurality of medical containers 100 may be secured to the conveyor 902 using an interaction between the notch 108 and locks or L-shaped locks (not shown) coupled to the conveyor 902. As the plurality of medical containers 100 move along the conveyor 902 in a direction generally represented by arrow 908, the scanner 904 scans a bar code 910 on the processing label 806 to determine when blood 912 was collected, for example. Based on when the blood was collected, the sorter 906 sorts the medical containers 100 such that higher priority medical containers 100 (e.g., less time until blood expiration) are processed sooner and/or identified to be processed sooner while lower priority medical containers 100 (e.g., more time until blood expiration) are processed later and/or identified to be processed later. Such an approach, effectively and automatically triages blood packs as they enter a blood center, for example.

Figure 10:
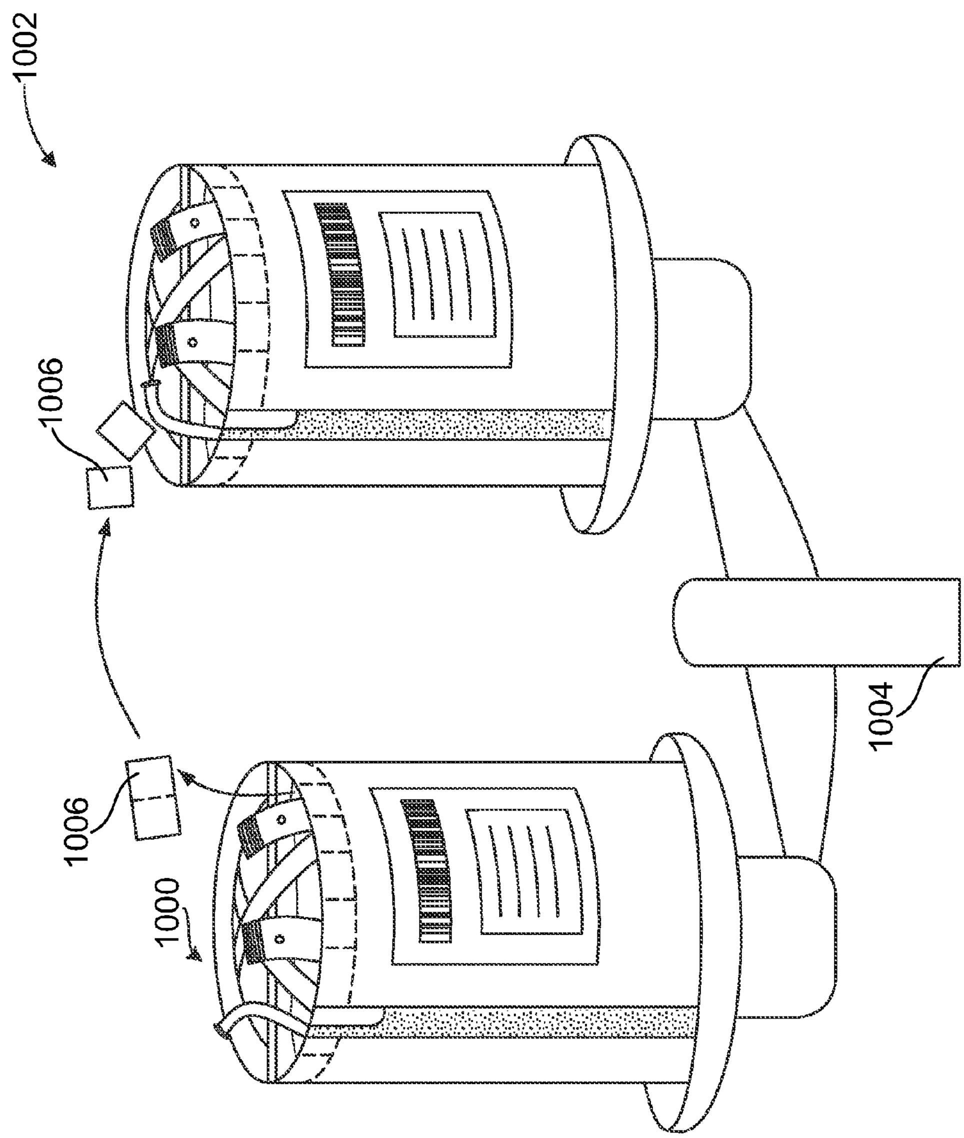
FIG. 10 depicts a plurality of the example medical containers being balanced prior to centrifugation.

FIG. 10 depicts a first medical container or prepackaged blood pack 1000 containing blood and a second medical container or prepackaged blood pack 1002 containing blood being balanced on a scale 1004 prior to centrifugation, for example. Because in this example the first medical container 1000 is slightly heavier than the second medical container 1002, removable tabs or tabs 1006 are being removed from the first medical container 1000 and being added to the second medical container 1002. Removing tabs 1006 from the first medical container 1000 decreases the weight of the first medical container 1000 and adding tabs 1006 to the second medical container 1002 increases the weight of the second medical container 1002.

Figure 11:
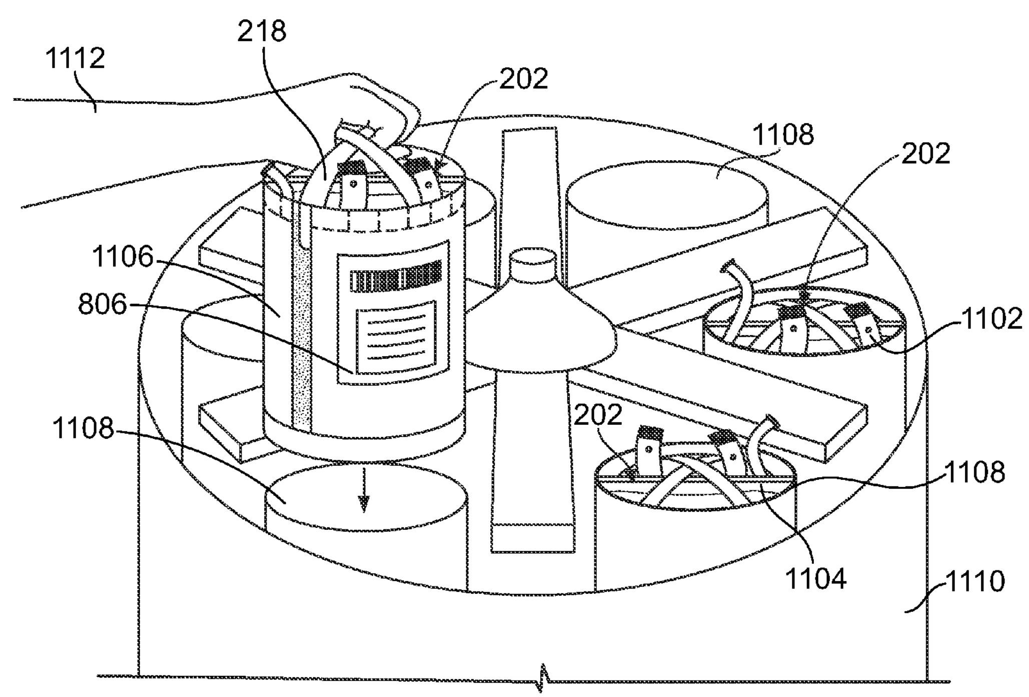
FIG. 11 depicts a plurality of the example medical containers being loaded into a centrifuge.

FIG. 11 depicts a plurality of medical containers 1102, 1104 and 1106 being loaded into cups 1108 of a centrifuge 1110. Because the medical containers 1102-1106 are provided with the straps 218, a person 1112 may relatively easily load and/or unload the centrifuge 1110 with the medical containers 1102-1106. Prior to or after centrifugation, the person 1112 may affix a label or an identifier adjacent to or on the processing label 806 that indicates and/or identifies the particular centrifuge used, for example. In contrast to known methods of positioning blood packs (not shown) into the cups 1108 and/or liners (e.g., tubes or cylinder) in which a person has to be extremely careful when loading and/or unloading the blood packs to prevent breakage and/or disruption of an interface between the RBCs and plasma, the medical containers 1102-1106 are sized (e.g., a cylindrical shape) to correspond to the cups 1108 and the blood packs 202 are positioned within the respective medical container 1102-1106 throughout a majority of blood collection and/or processing. Such an approach of integrating the blood pack 202 into the medical containers 1102-1106 decreases the amount of time spent loading and/or unloading the centrifuge 111 with the medical containers 1102-1106 and/or loading and/or unloading liners with blood packs. Additionally, integrating the blood pack 202 into the medical containers 1102-1106 decreases the amount of operator handling and, thus, the amount of accidents in which blood packs 202 break and/or decreases the number of instances in which an interface between the RBCs and plasma is disrupted after centrifugation.

Figure 12:
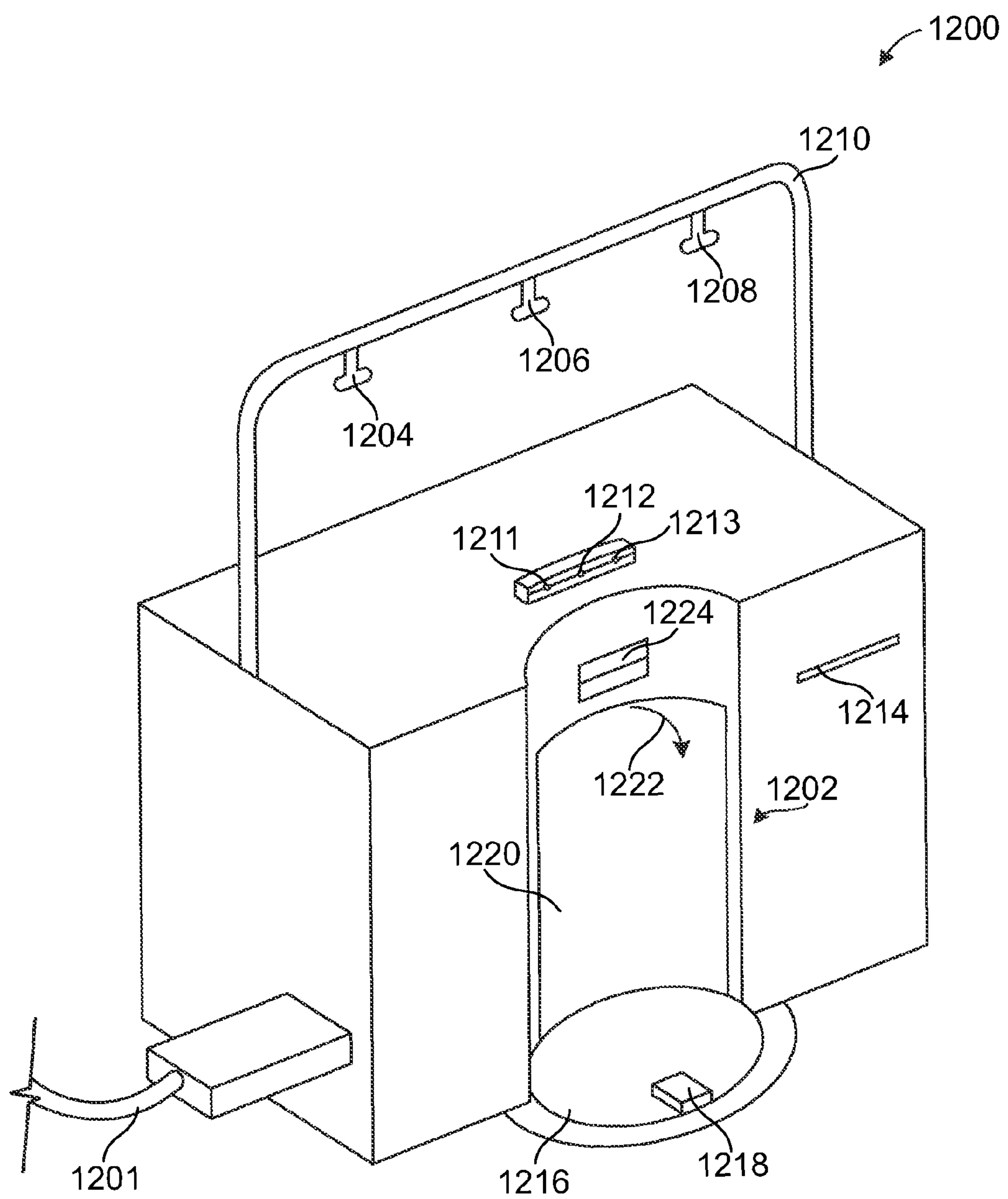
FIGS. 12-15 depict various views of an example expressor used during blood processing.

FIG. 12 depicts an example expressor, plasma expressor device or apparatus 1200 that may be communicatively coupled to a computer or other processing or data storage device (not shown) via a plug 1201, for example. The expressor 1200 may be used during blood processing to force different blood components from the container 206 during processes that separate plasma from whole blood and/or to remove white blood cells from red blood cells (RBCs), for example. The expressor 1200 includes a loading station 1202 in which the medical container 100 containing centrifuged blood may be positioned. A plurality of hangers or hooks 1204-1208 may be coupled to and/or supported by a frame 1210 from which the transfer bags and/or the container containing the preservative solution may be suspended. The expressor 1200 includes first through third clamps or fluid control devices 1211-1213 to control the flow of fluid between the container 206, the transfer bags and/or the container containing the preservative solution, for example. Additionally, the expressor 1200 includes a printer (e.g., a label printer) 1214 to print labels containing information associated with the contents of the medical container 100, the container 206 and/or the transfer bags, for example. Because these labels may be affixed directly to the transfer bags (e.g., a final blood component), the labels printed by the printer 1214 may comply with blood industry, ISBT 128 and/or FDA regulation.

The loading station 1202 includes a base 1216 having a lock or L-shaped lock 1218 that corresponds to the notch 108 to secure the medical container 100 relative to the expressor 1200. A portion 1220 of the loading station 1202 may pivot in a direction generally indicated by arrow 1222 to compress the medical container 100 to remove blood components (e.g., plasma or RBCs) from the container 206. The portion 1220 may be spring loaded and may be rotated and/or moved using any mechanical device (e.g., a motor, an actuator) (not shown). Additionally or alternatively, the loading station 1202 may include a sensor 1224 that may read a portion of the processing label 604 (e.g., the bar code 606) to identify information associated with the particular medical container 100, for example.

Figure 13:
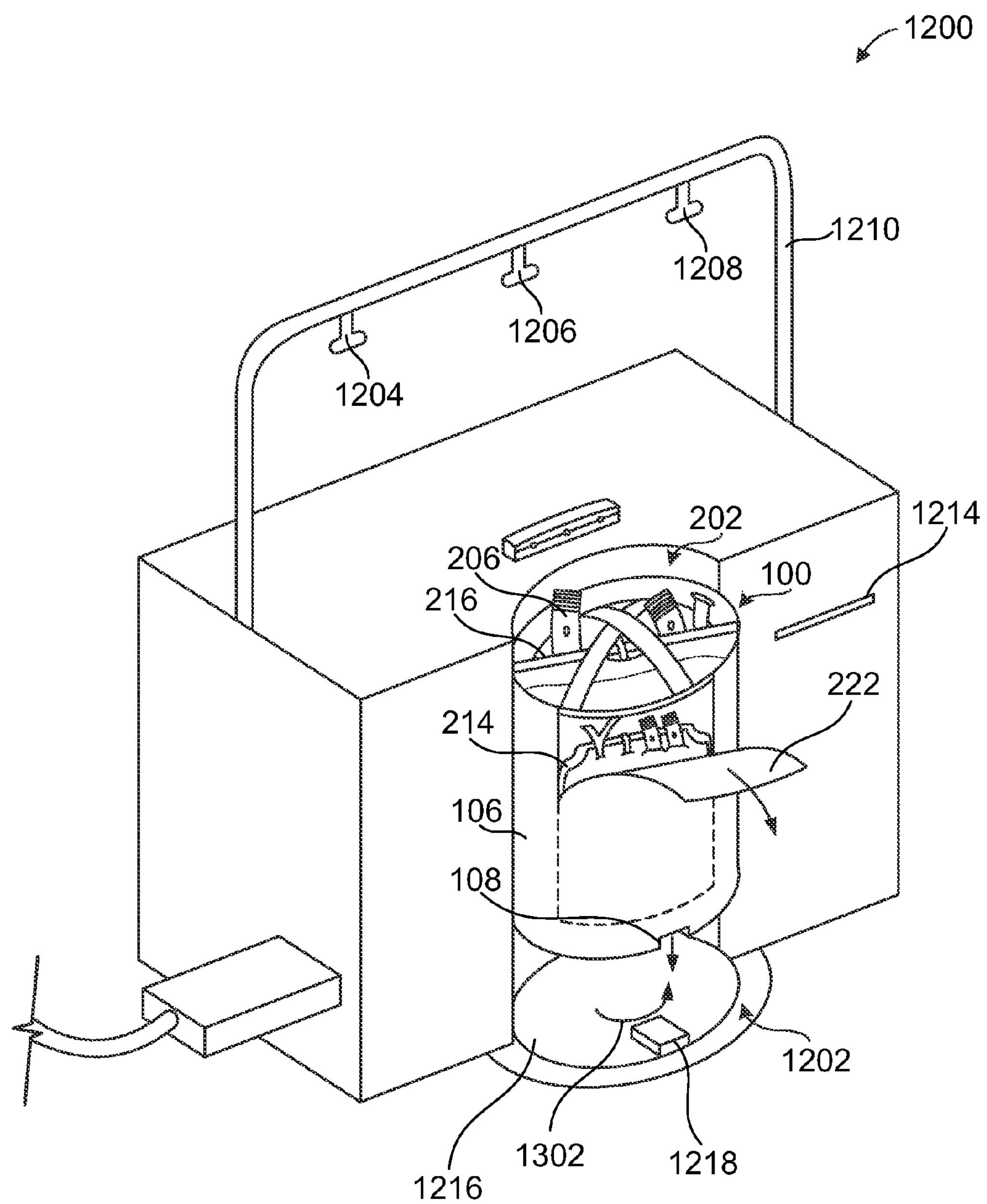
Figure 14:
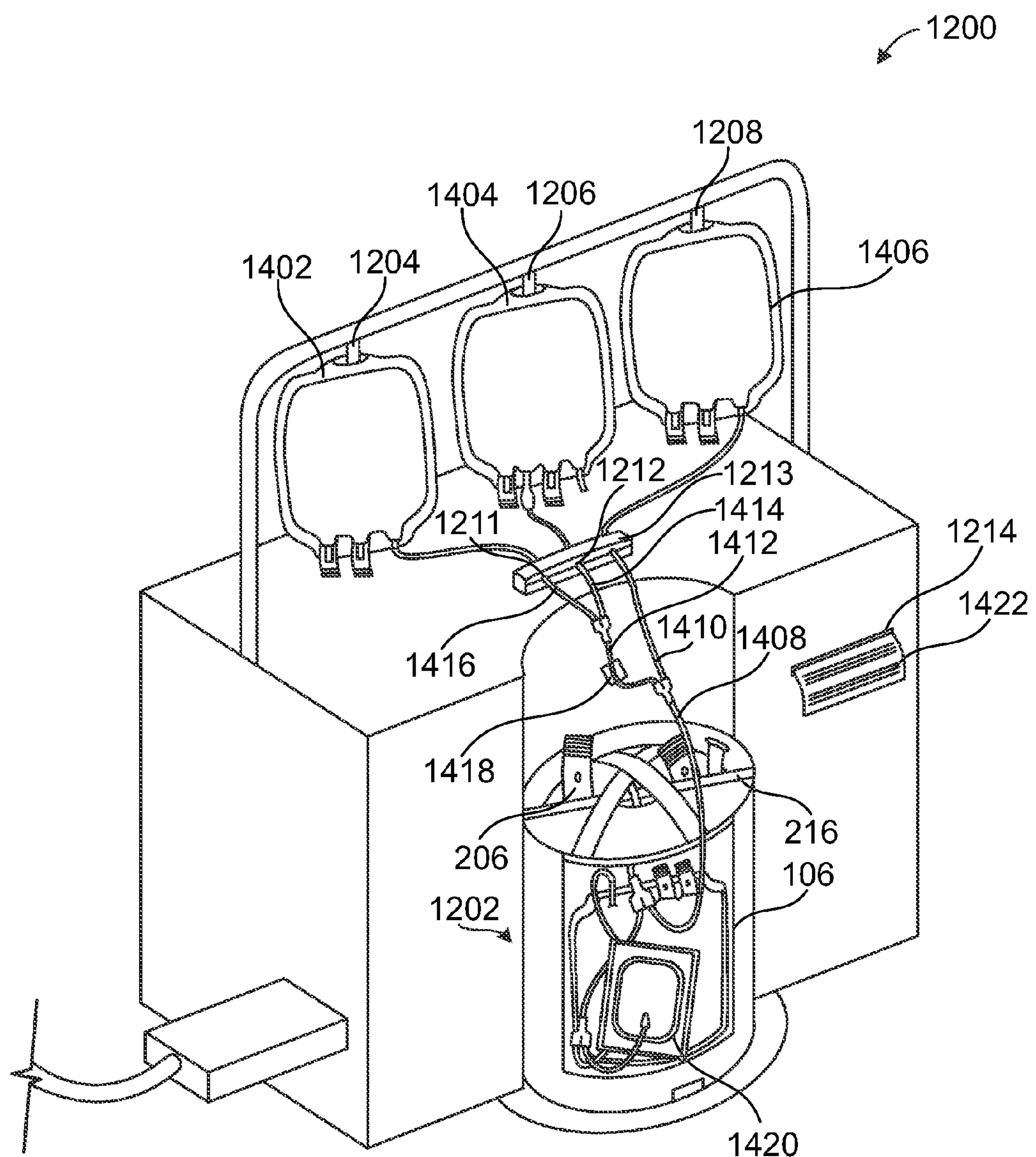

FIGS. 13 and 14 depict the expressor 1200 and the medical container 100. FIG. 13 depicts the medical container 100 being loaded into the loading station 1202 and the portion 222 of the elongated body 106 being removed to provide access to transfer packs positioned within the second storage compartment 214, for example. To secure the medical container 100 relative to the expressor 1200, a person may position the medical container 100 such that the L-shaped lock 1218 enters the notch 108 and then the medical container 100 may be rotated in a direction generally represented by arrow 1302 to secure the medical container 100.

Figure 15:
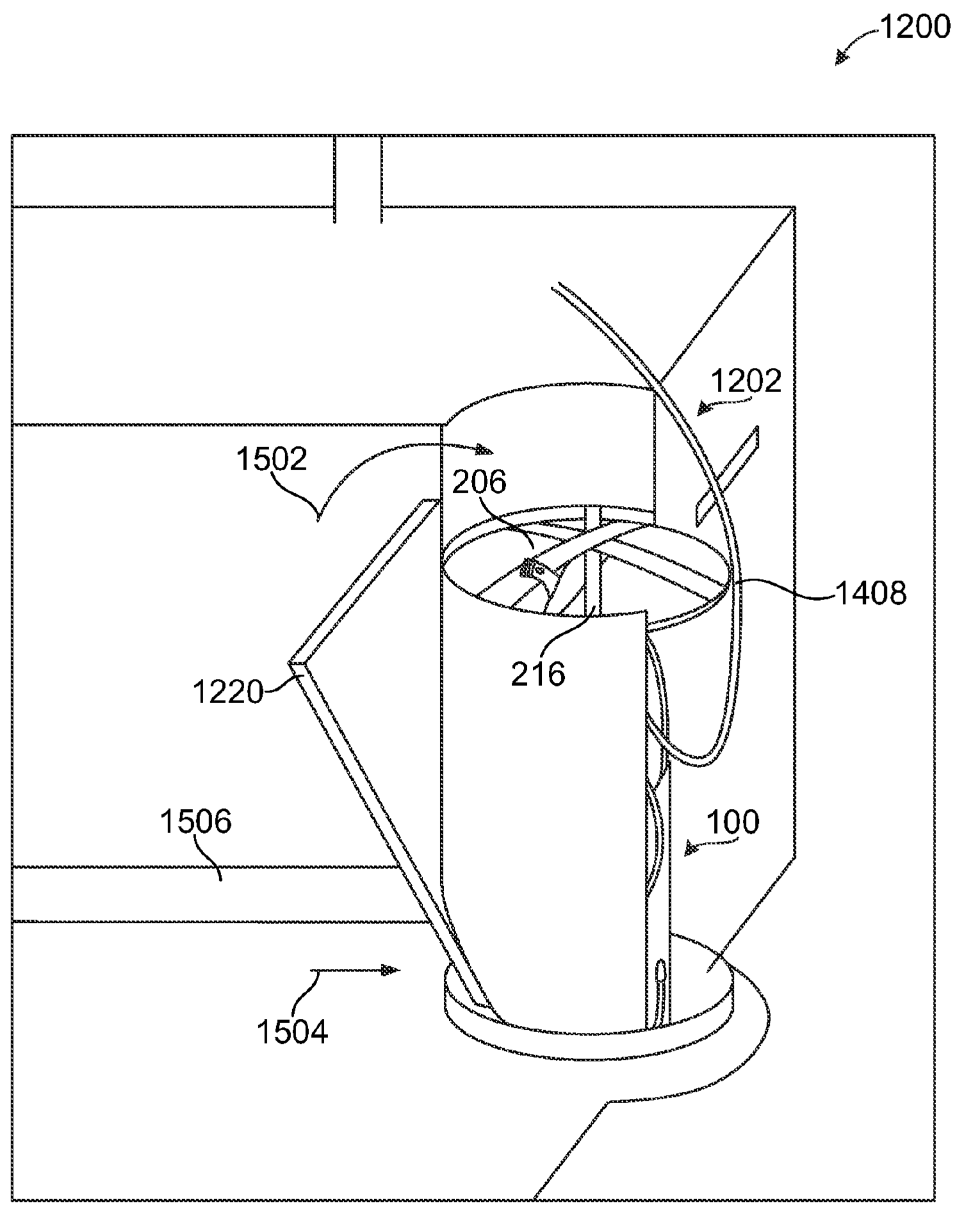

Turning to FIG. 14, after the portion 222 has been removed from the medical container 100, a first transfer bag 1402, a container 1404 containing preservative solution and a second transfer bag 1406 may be hung on the respective hanger 1204, 1206 and 1208. Additionally, tubes 1408, 1410, 1412, 1414, and 1416 may be at least partially positioned in the clamps 1211-1213. Turning to FIG. 15, once the medical container 100 is secured in the loading station 1202 and the transfer bags 1402 and 1406 and the container 1404 containing the preservative solution are hung from the respective hangers 1204-1208, the portion 1220 of the loading station 1202 may be moved and/or extended in a direction generally represented by arrows 1502 and/or 1504 via an extender or rod 1506. As the portion 1220 moves, the container 206 compresses against the divider 216 pushing plasma from the container 206 through the tube 1408. Because initially the second and third clamps 1212 and 1213 may be closed preventing fluid flow through the tubes 1410 and 1414 and the first clamp 1211 may be open, the plasma may flow through the tubes 1408, 1412 and 1416 to be stored in the first transfer bag 1402.

A sensor 1418 (e.g., a hematocrit sensor, a light sensor, an opaque sensor, a light density sensor or any other type of sensor that can determine light density of the fluid) communicatively coupled to the clamps 1211, 1212 and/or 1213 may be positioned adjacent the tube 1412 to detect whether plasma or RBCs are flowing through the tube 1412, for example. Once the sensor 1418 detects RBCs flowing through the tube 1412, a signal may be conveyed to the first clamp 1211 to close substantially preventing additional fluid flow through the tube 1416 to the first transfer bag 1402 and for the second clamp 1212 to open enabling the preservative solution to flow from the container 1404 through the tubes 1408, 1412 and 1414 to the container 206. As the preservative solution flows into the container 206, the preservative solution may mix with the RBCs. The preservative solution may be Adosol®, E-SOL or any other suitable additive.

After the preservative solution has been added to the container 206, the second clamp 1212 may close substantially preventing additional fluid flow through the tube 1414 and third clamp 1213 may open enabling fluid flow through the tube 1410. A pump (not shown) and/or the portion 1220 may further compress the container 206 through the medical container 100 to flow the RBCs through a filter (a leukocyte filter) 1420 and then through the tubes 1408 and 1410 to be stored in the second transfer bag 1406. Because the elongated body 106 is made of a relatively flexible material, the portion 1220 may compress the container 206 through the medical container 100 itself, thereby eliminating the need to remove the container 206 from the medical container 100. After the RBCs have been transferred through the filter 1420 to the second transfer bag 1406, the printer 1214 may print a label(s) (one of which is represented by reference number 1422) using information obtained from the processing label 604, for example. The label may then be affixed to the first transfer bag 1402, for example.

Figure 16:
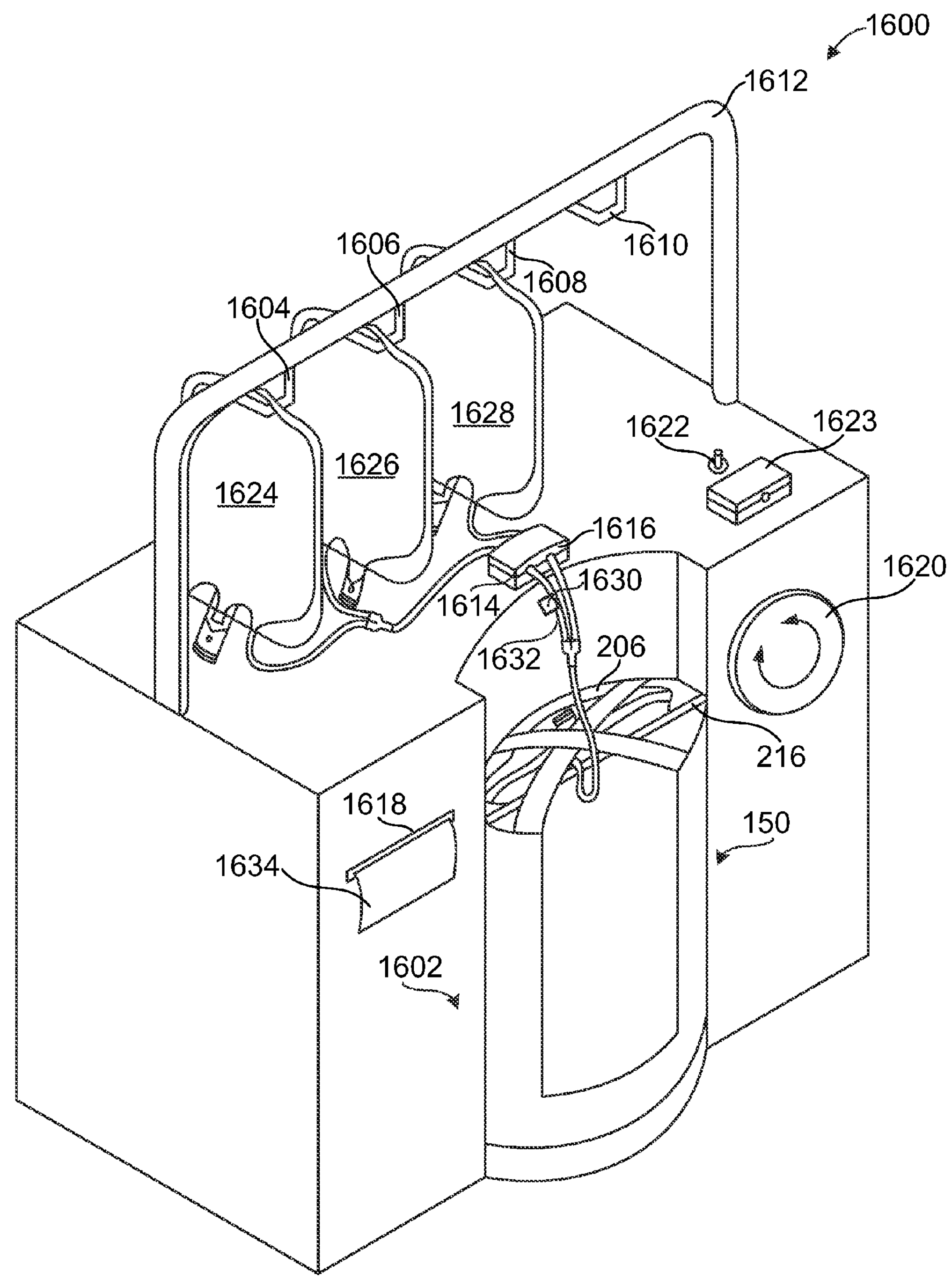
FIG. 16 depicts an alternative example expressor.

FIG. 16 depicts an alternative expressor 1600 that includes a loading station 1602 in which the medical container 150 containing centrifuged blood may be positioned. A plurality of hangers or hooks 1604-1610 may be coupled to and/or supported by a frame 1612 from which the transfer bags and/or the container containing the preservative solution may be suspended. The expressor 1600 includes first and second clamps or fluid control devices 1614 and 1616 to control the flow of fluid between the container 206, the transfer bags and/or the container containing the preservative solution, for example. The expressor 1600 includes a printer (e.g., a label printer) 1618 to print labels containing information associated with the contents of the medical container 100, the container 206 and/or the transfer bags, for example. The expressor 1600 includes a pump (e.g., a peristaltic pump) 1620 that may used to pump blood through a filter (not shown) during a leukoreduction process. Additionally, the expressor 1600 includes a sensor 1622 that may sense a pressure of the blood as it is being pumped through the filter and a fixture, fastener or clamp 1623 to secure a tube (not shown) to be connected to the sensor 1622 during the leukoreduction process.

As discussed above, once the medical container 150 is secured in the loading station 1602 and transfer bags 1624 and 1626 and a container 1628 containing preservative solution are hung from the respective hangers 1604-1608, a portion (e.g., similar to the portion 1220) of the loading station 1602 may be moved and/or extended to compress the container 206 against the divider 216 pushing plasma from the container 206. Because initially the second clamp 1616 may be closed preventing fluid flow to the container 1628 and the first clamp 1614 may be open, the plasma may flow into one of the transfer bags 1624 and 1626.

A sensor 1630 communicatively coupled to the clamps 1614 and/or 1616 may be positioned adjacent a tube 1632 to detect whether plasma or RBCs are flowing through the tube 1632, for example. Once the sensor 1630 detects RBCs flowing through the tube 1632, a signal may be conveyed to the first clamp 1614 to close substantially preventing additional fluid flow to the transfer bags 1624 and 1626 and for the second clamp 1616 to open enabling the preservative solution to flow from the container 1628 to the container 206. As the preservative solution flows into the container 206, the preservative solution may mix with the RBCs.

After the preservative solution has been added to the container 206, the container 206 may be removed from the medical container 150 and hung from the hanger 1610. Tubes (not shown) may be positioned adjacent the pump 1620 that moves (e.g., rotates) to urge the RBCs through a filter (not shown) (e.g., a leukocyte filter) and into another transfer bag (not shown) fluidly coupled to the container 206. Additionally, another tube (not shown) may be positioned adjacent the sensor 1622 to enable the sensor 1622 to sense the pressure of the blood flowing from the container 206 to the transfer bag and, thus, to enable the rate at which the pump 1620 pumps the RBCs from the container 206 to be adjusted accordingly. After the leukoreduction process is complete, the printer 1618 may print a label(s) (one of which is represented by reference number 1634) using information obtained from the processing label 604, for example. The label may then be affixed to the transfer bags 1624 and/or 1626 and/or the transfer bag containing RBCs, for example.

FIGS. 17-22 depict a portion (e.g., a side portion) 1700 of an example expressor 1702 and a portion of a blood pack 1704 during different stages of a leukoreduction process. The expressor 1702 includes a pump (e.g., a peristaltic pump) 1706, a sensor (e.g., a pressure sensor) 1708 and a sensor (e.g., an optical sensor) 1710 all or some of which may be communicatively coupled to the expressor 1702 and/or to one another. The blood pack 1704 includes a container 1712 containing RBCs and first through fourth tubes 1714-1720 fluidly coupling the container 1712 to a transfer bag 1722. The first tube 1714 is fluidly coupled to the second tube 1716 via a first Y-connector 1724, the second tube 1716 is fluidly coupled to the third tube 1718 via a filter (e.g., a WBC filter or a leukocyte filter) 1726 and the third tube 1718 is fluidly coupled to the fourth tube 1720 via a second Y-connector 1728. The blood pack 1704 additionally includes a fifth tube 1730 and a sixth tube 1732 between which a valve (e.g., a check valve) 1734 is positioned. The fifth tube 1730 is fluidly coupled to the first tube 1714 via the first Y-connector 1724 and the sixth tube 1732 is fluidly coupled to the fourth tube 1720 via the second Y-connector 1728.

Figures 17, 18, 19, 20, 21, 22:
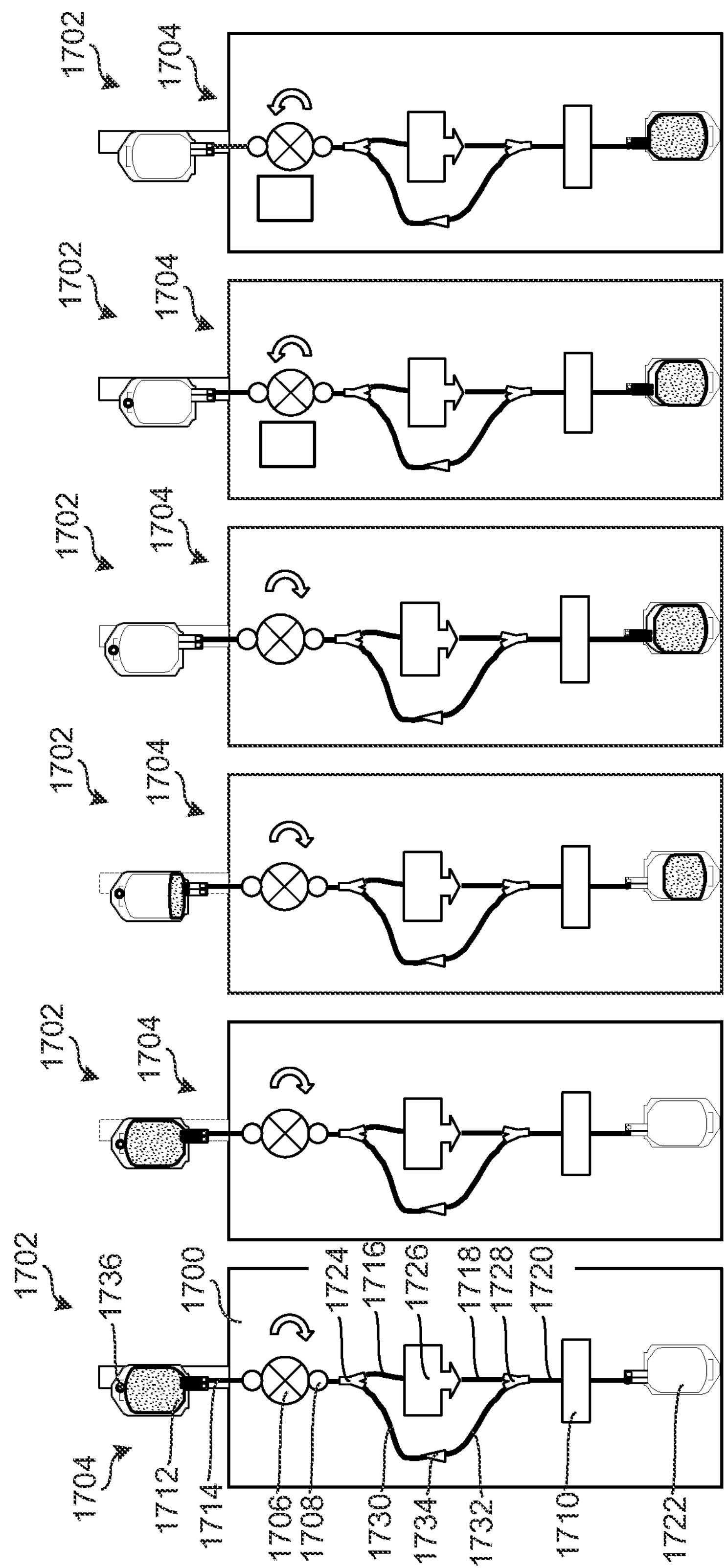
FIGS. 17-22 depict a leukoreduction process using another example expressor.

In operation, after the plasma has been removed from the container 1712 in a process as described above, for example, the container 1712 may be removed from the medical container (e.g., similar to medical container 100 and/or 150) and hung on a hanger 1736. The first tube 1714 may then be positioned adjacent the pump 1706 and the fourth tube 1720 may be positioned adjacent the sensor 1710. As shown in FIGS. 17-20, the pump 1706 may move (e.g., rotate) urging fluid from the container 1712 through the filter 1726 and into the transfer bag 1722. As the pump 1706 pumps the blood from the container 1712, the sensor 1708 may determine a pressure of the blood within the first tube 1714. Based on the pressure determined or measured by the sensor 1708, the expressor 1702 may change (e.g., decrease or increase) the rate at which the pump 1706 pumps the blood from the container 1712. As the blood flows through the fourth tube 1720, the sensor 1710 detects whether or not blood is flowing through the fourth tube 1720. If the sensor 1710 detects blood flowing through the fourth tube 1720, this may be indicative of additional blood upstream and/or in the container 1712 and, thus, the pump 1706 may continue to pump blood to the transfer bag 1722. However, if the sensor 1710 does not detect blood flowing through the fourth tube 1720, this may be indicative of no or limited additional blood upstream and/or in the container 1721 and, thus, the pump 1706 may reverse its direction, as shown in FIGS. 21 and 22 to remove air (e.g., burp) from the transfer bag 1722. The transfer bag 1722 may then be decoupled from the blood pack 1704. After the leukoreduction process is complete, a printer (e.g., similar to the printer 1214 or 1618) may print a label(s) using information obtained from the processing label 604 as described above, for example. The label may then be affixed to the transfer bag 1722 containing RBCs.

The flow diagrams depicted in FIGS. 23-26 are representative of machine readable instructions that can be executed to implement the examples described herein to collect and/or process blood. Such machine readable instructions may be executed at least in part by the apparatus 700, the triage system 900 and/or the expressor 1200, 1600 and/or 1702, for example. The example processes of FIGS. 23-26 may be performed using a processor, a controller and/or any other suitable processing device. For example, the example processes of FIGS. 23-26 may be implemented in coded instructions stored on a tangible medium such as a flash memory, a read-only memory (ROM) and/or random-access memory (RAM) associated with a processor. Alternatively, some or all of the example processes of FIGS. 23-26 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 23-26 may be implemented manually or as any combination(s) of any of the foregoing techniques, for example, any combination of firmware, software, discrete logic and/or hardware. Further, although the example processes of FIGS. 23-26 are described with reference to the flow diagrams of FIGS. 23-26, other methods of implementing the processes of FIGS. 23-26 may be employed. For example, the order of execution of the blocks may be changed, and/or some of the blocks described may be changed, eliminated, sub-divided, or combined. Additionally, any or all of the example processes of FIGS. 23-26 may be performed sequentially and/or in parallel by, for example, separate processing threads, processors, devices, discrete logic, circuits, etc.

Figure 23:
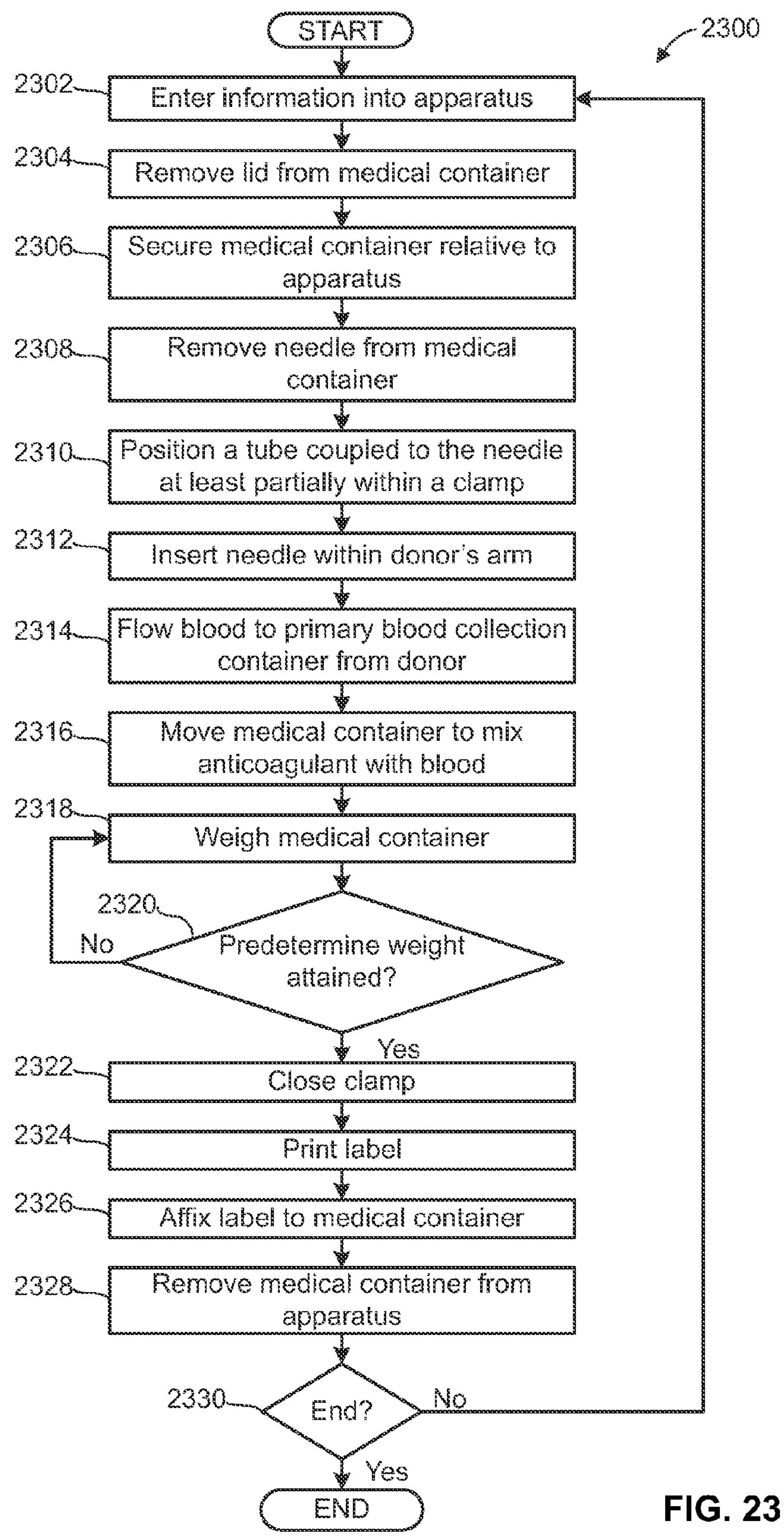
FIGS. 23-26 are flow diagrams representative of example processes that may be executed using the examples described herein.

Turning to FIG. 23, a method 2300 may begin by having and/or prompting an operator to enter information into the apparatus 700 (FIG. 7) (block 2302). The information may be related to a donor, the operator or any other information associated with the blood collection. The operator may then remove the lid 104 (FIG. 1A) from the medical container 100 (FIG. 1A) (block 2304) and secure the medical container 100 (FIG. 1A) relative to the apparatus 700 (FIG. 7) (block 2306). The medical container 100 (FIG. 1A) may be secured relative to the apparatus 700 (FIG. 7) by an interaction between the notch 108 (FIG. 1A) and the L-shaped lock 716 (FIG. 7) of the apparatus 700 (FIG. 7). The operator may then remove the needle 204 (FIG. 2) from the first storage compartment 212 (FIG. 2) of the medical container 100 (FIG. 1A) (block 2308)

and position the tube 208 fluidly coupled to the needle 204 (FIG. 2) at least partially within the clamp 802 (FIG. 8A) (block 2310).

The operator may then insert the needle 204 (FIG. 2) into the donor's arm 712 (FIG. 7) (block 2312) and blood may flow to the primary blood collection container 206 (FIG. 2) from the donor (block 2314). As the blood flows into the primary blood collection container 206 (FIG. 2), the apparatus 700 (FIG. 7) may move the medical container 100 (FIG. 1A) to mix anticoagulant contained in the primary blood collection container 206 (FIG. 2) with the blood (block 2316). The weight scale 706 (FIG. 7) may then weigh the medical container 100 (FIG. 1A) (block 2318) and the apparatus 700 (FIG. 7) and/or the computer 714 (FIG. 7) may determine if a predetermined weight has been attained (block 2320). Additionally or alternatively, if the apparatus 700 includes the pump 804 to pump blood from the donor, the pump 804 may convey to the apparatus 700 the amount of blood that has been pumped and the apparatus 700 (FIG. 7) and/or the computer 714 (FIG. 7) may determine if a predetermined amount of blood has been collected. If the apparatus 700 (FIG. 7) and/or the computer 714 (FIG. 7) determines that the predetermined weight and/or amount of blood has not been attained, control advances to block 2318.

However, if the apparatus 700 (FIG. 7) and/or the computer 714 (FIG. 7) determines that the predetermined weight and/or the amount of blood has been attained, control advances to block 2322 and a signal may be conveyed to the clamp 802 (FIG. 8A) causing the clamp 802 (FIG. 8A) to close (block 2322). Closing the clamp 802 (FIG. 8A) once the medical container 100 (FIG. 1A) weighs a predetermined amount and/or after a predetermined amount of blood has been collected substantially prevents over-collection of blood from the donor. The apparatus 700 may then print the processing label 806 (FIG. 8A) (block 2324). In some examples, the operator may initiate the printer 704 (FIG. 7) to print the processing label 806 (FIG. 8A) by pressing the button 718 (FIG. 7). The operator may then affix the processing label 806 (FIG. 8A) to the medical container 100 (FIG. 1A) (block 2326) and remove the medical container 100 (FIG. 1A) from the apparatus 700 (FIG. 7) (block 2328). The method 2300 then determines if it should advance to block 2302 (block 2330). Otherwise the example method is ended.

Figure 24:
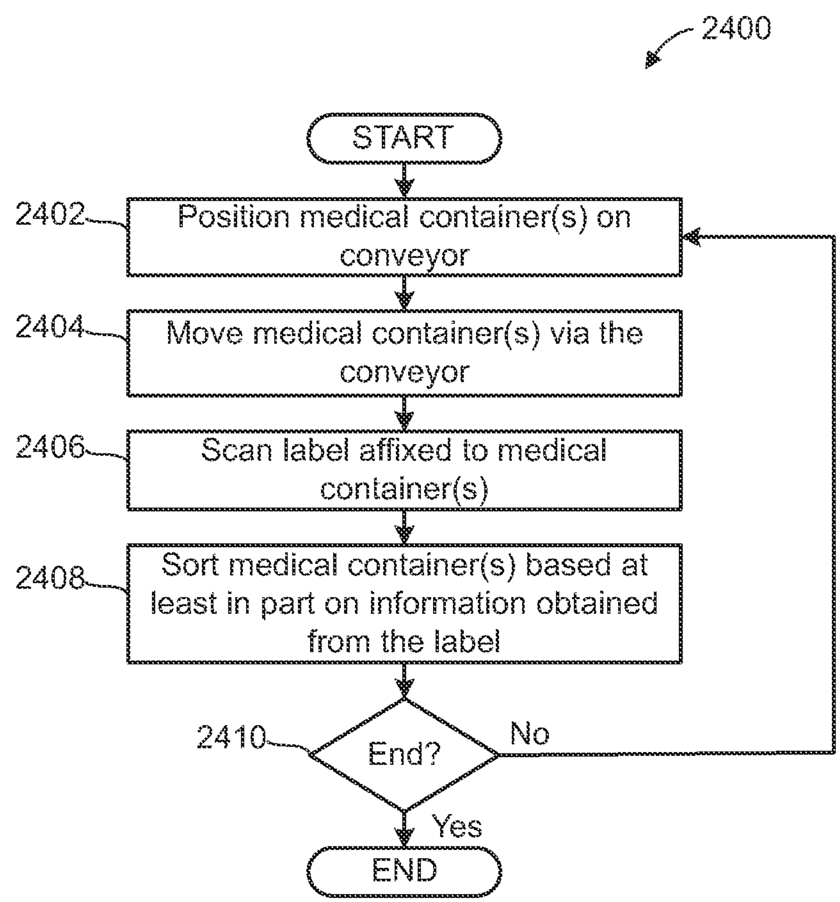

Turning to FIG. 24, a method 2400 may begin by positioning the medical container(s) 100 (FIG. 1A) on the conveyor 902 (FIG. 9) (block 2402). The medical container(s) 100 (FIG. 1A) may be secured to the conveyor 902 (FIG. 9) using an interaction between the notch 108 (FIG. 1A) and the locks coupled to the conveyor 902 (FIG. 9). As the medical container(s) 100 (FIG. 1A) moves along or on the conveyor 902 (FIG. 9) (block 2404), the scanner 904 scans the processing label 806 (FIG. 8A) affixed to the medical container 100 (FIG. 1A) (block 2406). By scanning the processing label 806 (FIG. 8A), the example triage system 900 (FIG. 9) may determine when the blood 912 (FIG. 9) was collected from information included on the processing label 806 (FIG. 8A). The sorter 906 (FIG. 9) may then sort the medical container(s) 100 (FIG. 1A) based at least in part on information obtained from the processing label 806 (FIG. 8A) (block 2408). The method 2400 then determines if it should advance to block 2402 (block 2410). Otherwise the example method is ended.

Figure 25:
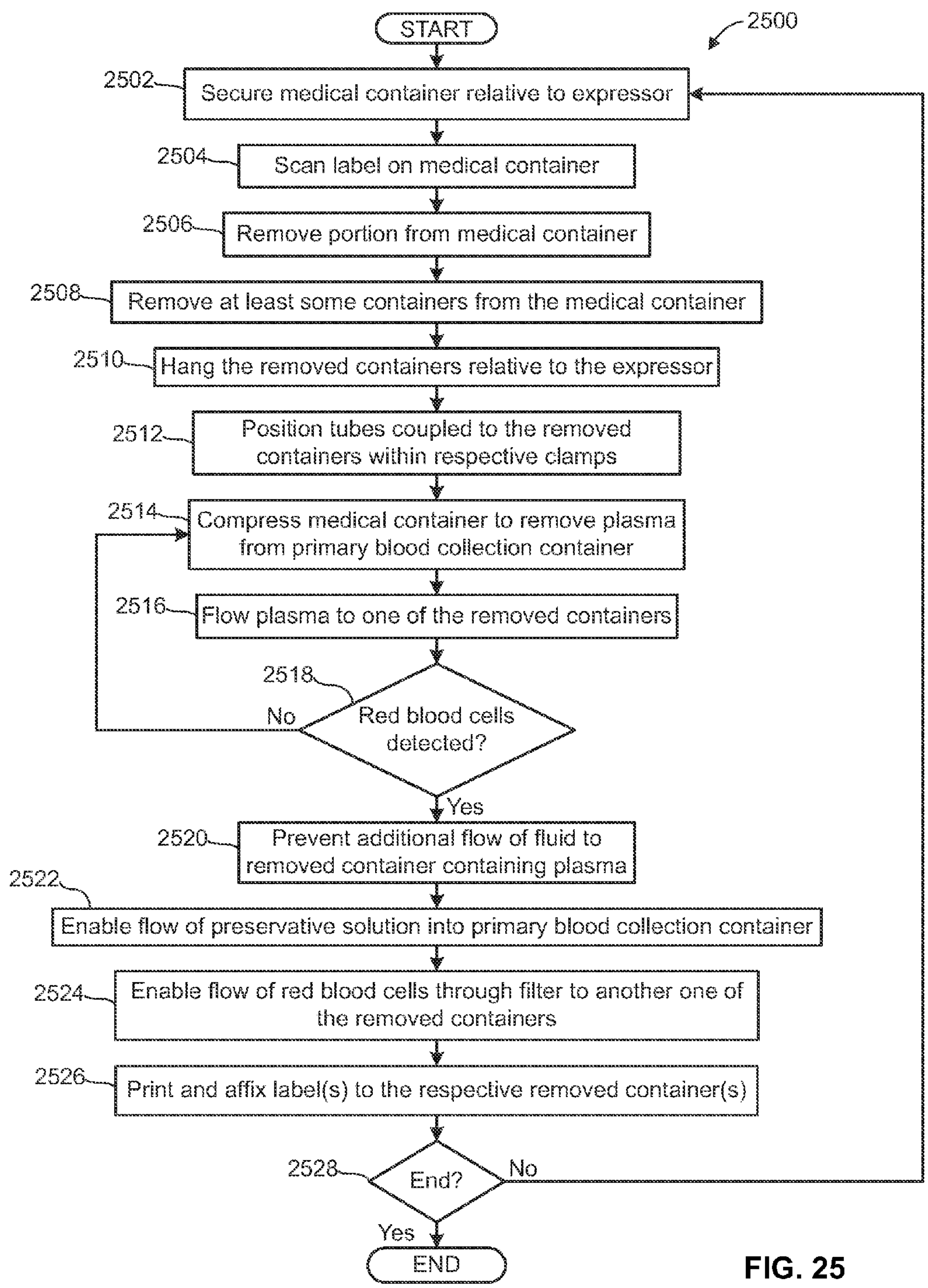

Turning to FIG. 25, an example method 2500 may begin by securing the medical container 100 (FIG. 1A) relative to the expressor 1200 (FIG. 12) (block 2502) and the sensor 1224 (FIG. 12) may scan the processing label 806 (FIG. 8A) on the medical container 100 (FIG. 1A) (block 2504). By scanning the processing label 806 (FIG. 8A), the expressor 1200 may obtain information associated with the medical container 100 (FIG. 1A) and/or the contents of the medical container 100 (FIG. 1A). An operator may then remove the portion 222 (FIG. 2) from the medical container 100 (FIG. 1A) (block 2506) to gain access to at least some containers (e.g., transfer bags) positioned within the second storage compartment 214 (FIG. 2), for example.

The operator may then remove at least some of the containers (e.g., the first transfer bag 1402, the container 1404 containing preservative solution and the second transfer bag 1406) from the medical container 100 (FIG. 1A) (block 2508) and the removed containers may be hung on the respective hangers 1204-1208 (block 2510). The tubes 1408-1416 coupled to the removed containers may then be positioned within the respective clamps 1211-1213 (FIG. 12) (block 2512).

The expressor 1200 (FIG. 12) may then compress the medical container 100 (FIG. 1A) to remove plasma from the primary blood collection container 206 (FIG. 2) (block 2514) by compressing the primary blood collection container 206 (FIG. 2) against the divider 216 (FIG. 2). As the medical container 100 (FIG. 1A) and the primary blood collection container 206 (FIG. 2) are compressed, plasma may flow to one of the removed containers (e.g., the first transfer bag 1402) (block 2516) and the sensor 1418 may detect for red blood cells (block 2518) flowing through the tube 1412. If red blood cells are not detected, control advances to block 2514.

However, if red blood cells are detected, control advances to block 2520 and additional fluid flow is prevented to the container containing plasma (block 2520). To prevent additional fluid flow to the container containing plasma, a signal may be conveyed to the first clamp 1211 to close, thereby substantially preventing additional fluid flow through the tube 1416 to the first transfer bag 1402. Additionally, a signal may be conveyed to the second clamp 1212 causing the second clamp 1212 to open enabling the preservative solution to flow from the container 1404 through the tubes 1408, 1412 and 1414 into the primary blood collection container 206 (FIG. 2) (block 2522). As the preservative solution flows into the primary blood collection container 206, the preservative solution may mix with the red blood cells within the primary blood collection container 206.

The expressor 1200 (FIG. 12) may then enable the flow of red blood cells through the filter 1420 (FIG. 14) to another one of the removed containers (e.g., the second transfer bag 1406) (block 2524). Specifically, to enable fluid flow to the other removed container, the second clamp 1212 may close substantially preventing additional fluid flow through the tube 1414 and the third clamp 1213 may open enabling fluid flow through the tube 1410 and a pump and/or the portion 1220 (FIG. 12) may further compress the primary blood collection container 206 (FIG. 2) through the medical container 100 to flow the red blood cells through the filter 1420 and then through the tubes 1408 and 1410 to be stored in the second transfer bag 1406. The expressor 1200 (FIG. 12) may then print labels that may be affixed to the respective removed containers (e.g., the first and second transfer bags 1402 and 1406) (block 2526). The labels may be printed using at least some information obtained from scanning the processing label 806 (FIG. 8A). The method 2500 then determines if it should advance to block 2502 (block 2528). Otherwise the example method is ended.

Figure 26:
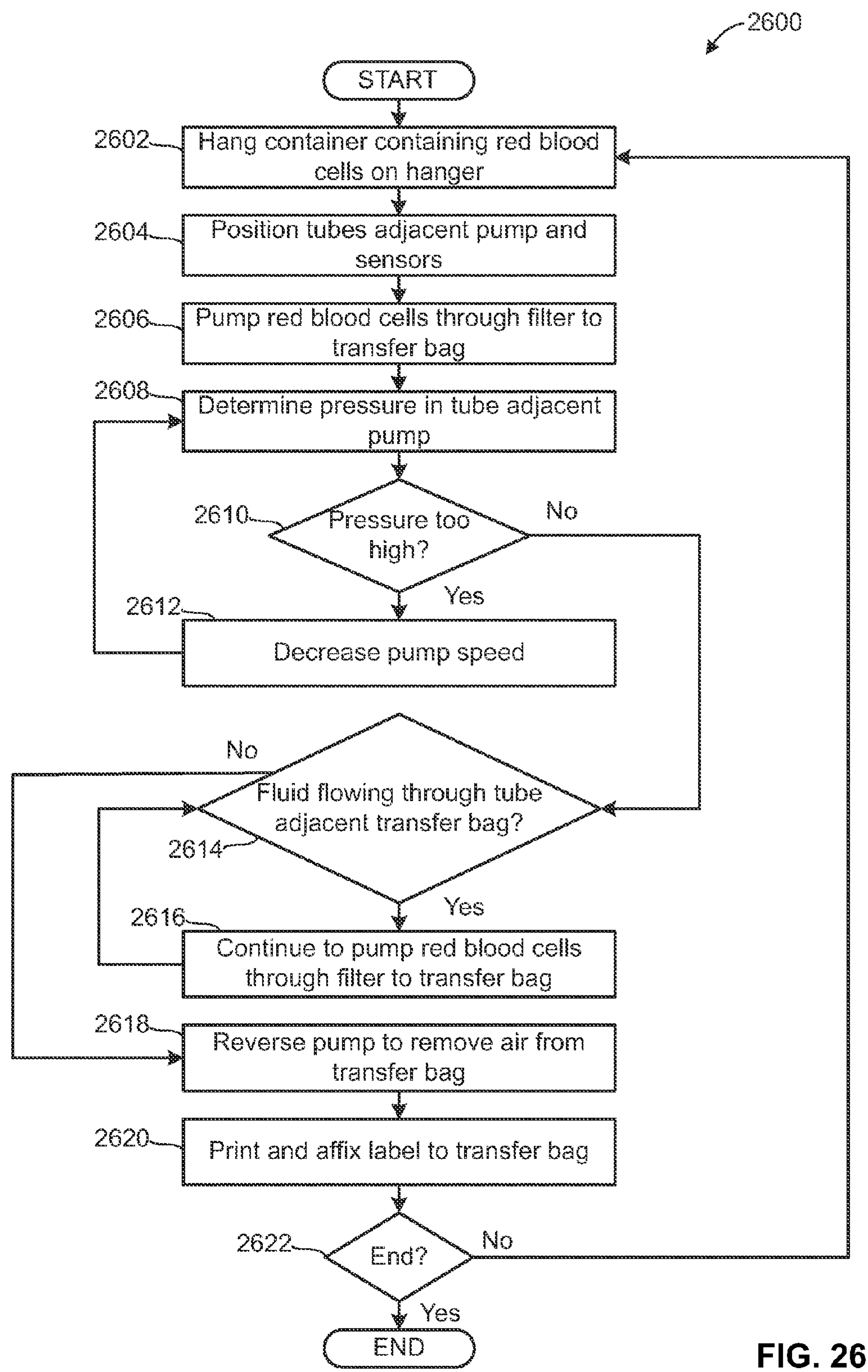

Turning to FIG. 26, an example method 2600 may begin by hanging the container 1712 (FIG. 17) on the hanger 1736 (FIG. 17) (block 2602) and positioning the respective tubes 1714 and 1720 (FIG. 17) adjacent the pump 1706 (FIG. 17) and/or the sensors 1708 (FIG. 17) and/or 1710 (FIG. 17)

(block 2604). The pump 1706 (FIG. 17) may then pump the blood from the container 1712 (FIG. 17) through the filter 1726 (FIG. 17) and into the transfer bag 1722 (FIG. 17) (block 2606). As the pump 1706 (FIG. 17) pumps the blood from the container 1712 (FIG. 17), the sensor 1708 (FIG. 17) may determine a pressure of the blood within the first tube 1714 (FIG. 17) adjacent the pump 1706 (FIG. 17) (block 2608). The expressor 1700 (FIG. 17) may then determine whether or not the pressure is too high (block 2610). If the expressor 1700 (FIG. 17) determines that the pressure is too high, control advances to block 2612 and the speed of the pump 1706 (FIG. 17) is decreased (block 2612).

However, if the expressor 1700 (FIG. 17) determines that the pressure is not too high, control advances to block 2614 and the sensor 1710 (FIG. 17) detects whether or not blood is flowing through the fourth tube 1720 (FIG. 17) adjacent the transfer bag 1722 (FIG. 17) (block 2614). If the sensor 1710 (FIG. 17) detects blood flowing through the fourth tube 1720 (FIG. 17) adjacent the transfer bag 1722 (FIG. 17), control advances to block 2616 and the pump 1706 (FIG. 17) continues to pump the blood from the container 1712 (FIG. 17) through the filter 1726 (FIG. 17) and into the transfer bag 1722 (FIG. 17) (block 2616). However, if the sensor 1710 (FIG. 17) does not detect blood flowing through the fourth tube 1720 (FIG. 17) adjacent the transfer bag 1722 (FIG. 17), control advances to block 2618 and the pump 1706 (FIG. 17) may reverse its direction to remove air from the transfer bag 1722 (block 2618). The expressor 1700 (FIG. 17) may then a print label(s) that may be affixed to the transfer bag 1722 (FIG. 17) (block 2620). The method 2600 then determines if it should advance to block 2602 (block 2622). Otherwise the example method is ended.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed:

1. A medical container configured to accommodate blood pack components during blood collection and processing, the medical container comprising:

an elongated body extending between first and second ends and defining a compartment;

a base fixedly secured to the first end of the elongated body;

a substantially planar divider extending through the compartment from the base to the second end of the elongated body to separate the compartment into a first subcompartment and a second subcompartment, the divider comprising a first material, the elongated body comprising a second material, and the base comprising a third material, the first and third materials being generally rigid and the second material being generally flexible, and the first subcompartment and the second subcompartment each being configured to accommodate blood pack components; and blood pack components comprising a primary blood collection container and one or more of a needle, one or more transfer bags, a leukocyte filter, or a container containing a preservative solution, wherein one or more of the blood pack components are fluidly coupled together, with the primary blood collection container being at least partially positioned in the first subcompartment and said one or more of the needle, the one or more transfer bags, the leukocyte filter, or the container containing the preservative solution being positioned in the second subcompartment.

2. The medical container of claim 1, wherein the divider is coupled to the base to increase the structural rigidity of the medical container.

3. The medical container of claim 2, wherein a portion of the elongated body is sufficiently deformable to be deformed toward the divider during a blood processing procedure.

4. The medical container of claim 1 configured for receipt within a centrifuge receptacle during blood processing, the medical container having a shape that is complementary to a shape of the centrifuge receptacle.

5. The medical container of claim 1, wherein the base further comprises a fixture to enable the medical container to be secured to another apparatus.

6. The medical container of claim 5, wherein the fixture comprises a slot to receive an L-shaped lock of the apparatus.

7. The medical container of claim 5, wherein the apparatus comprises at least one of a blood collection apparatus, or a plasma expressor used during blood processing.

8. The medical container of claim 1, further comprising a lid removably coupled at a second end of the elongated body, the lid to substantially prevent contaminants from entering the compartment.

9. The medical container of claim 8, wherein the lid comprises at least one of an aluminum lidding foil or plastic.

10. The medical container of claim 8, wherein the lid comprises a tab to facilitate removing the lid from the elongated body.

11. The medical container of claim 1, wherein the elongated body comprises one or more removable tabs to facilitate balancing the medical container with another medical container prior to centrifugation.

12. The medical container of claim 1, wherein the second material comprises at least one of a foil based material or a plastic material.

13. The medical container of claim 1, further comprising one or more straps coupled adjacent to a second end of the elongated body.

14. The medical container of claim 13, wherein the one or more straps are to secure the blood pack components within the first and second compartments.

15. The medical container of claim 13, wherein the one or more straps are to facilitate handling the medical container.

16. The medical container of claim 1, wherein the elongated body comprises a tearable portion to enable removal of one or more of the blood pack components from the second compartment.

17. The medical container of claim 1, wherein the elongated body comprises a transparent portion to enable a fluid level within the primary collection bag of the blood pack components to be identified.

18. The medical container of claim 1, further comprising a processing label to be affixed to the medical container in a location being exempt from regulatory requirements, the processing label comprising a machine readable portion and a human readable portion.

19. The medical container of claim 18, the machine readable portion to be scanned by a plasma expressor to facilitate printing other processing labels to be affixed to one or more transfer bags of the blood pack components after blood component separation, the other processing labels complying with regulatory requirements.

20. The medical container of claim 18, the machine readable portion to be scanned by a scanner of a triage system to facilitate triaging the medical container based on a priority level.

21. The medical container of claim 18, wherein the processing label is printed by at least one of a blood collection apparatus and a plasma expressor during the blood collection and processing.

22. The medical container of claim 1, further comprising a processing label to be affixed to the medical container in a location complying with regulatory requirements.

23. A medical container comprising:

an elongated body defining a compartment;

a base coupled at a first end of the elongated body;

a divider extending through the compartment to separate the compartment into a first subcompartment and a second subcompartment, the divider comprising a first material and the elongated body comprising a second material, the first material being generally rigid and the second material being generally flexible, and the first subcompartment and the second subcompartment each being configured to accommodate blood pack components; and blood pack components comprising a primary blood collection container and one or more of a needle, one or more transfer bags, a leukocyte filter, or a container containing a preservative solution, wherein one or more of the blood pack components are fluidly coupled together, with the primary blood collection container being at least partially positioned in the first subcompartment and said one or more of the needle, the one or more transfer bags, the leukocyte filter, or the container containing the preservative solution being positioned in the second subcompartment.

24. The medical container of claim 23, wherein the divider is coupled to the base to increase the structural rigidity of the medical container.

25. The medical container of claim 24, wherein a portion of the elongated body is sufficiently deformable to be deformed toward the divider during a blood processing procedure.

26. The medical container of claim 23 configured for receipt within a centrifuge receptacle during blood processing, the medical container having a shape that is complementary to a shape of the centrifuge receptacle.

27. The medical container of claim 23, wherein the base further comprises a fixture to enable the medical container to be secured to another apparatus.

28. The medical container of claim 27, wherein the fixture comprises a slot to receive an L-shaped lock of the apparatus.

29. A medical container configured to accommodate blood pack components and to be used in combination with at least one of a blood collection apparatus, a plasma expressor, and/or a conveyor during blood collection and processing, the medical container comprising:

an elongated body defining a compartment, the compartment being configured to accommodate blood pack components a divider extending through the compartment to separate the compartment into a first subcompartment and a second subcompartment;

a base coupled at a first end of the elongated body and an open or openable end at the opposite end of the elongated body, the base comprising a fixture to enable the medical container to be secured relative to at least one of a blood collection apparatus, a plasma expressor, and/or a conveyor during the blood collection and processing, wherein the fixture comprises a slot defined in the base and having a generally vertical portion associated with a bottom surface of the base and a generally horizontal portion associated with the generally vertical portion and spaced away from the bottom surface of the base, wherein the generally vertical portion of the slot extends to the perimeter of the base and a portion of the base is positioned between the perimeter of the base and the generally horizontal portion of the slot, such that the generally horizontal portion of the slot is spaced away from the perimeter of the base; and blood pack components comprising a primary blood collection container and one or more of a needle, one or more transfer bags, a leukocyte filter, or a container containing a preservative solution, wherein one or more of the blood pack components are fluidly coupled together, with the primary blood collection container being at least partially positioned in the first subcompartment and said one or more of the needle, the one or more transfer bags, the leukocyte filter, or the container containing the preservative solution being positioned in the second subcompartment.

30. The medical container of claim 29, wherein the fixture is configured to receive an L-shaped lock of the at least one of the blood collection apparatus, the plasma expressor, or the conveyor of associated with the triage system.

* * * * *